US012779031B2

(12) United States Patent
Almansour

(10) Patent No.: US 12,779,031 B2
(45) **Date of Patent: *Nov. 3, 2026**

(54) IMMUNIZATION METHOD AGAINST INFECTION BY SARS-CoV-2

(71) Applicant: Imam Abdulrahman Bin Faisal University, Dammam (SA)

(72) Inventor: Iman Almansour, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

This patent is subject to a terminal disclaimer.

(21) Appl. No.: 19/397,109

(22) Filed: Nov. 21, 2025

(65) Prior Publication Data

US 2026/0077035 A1 Mar. 19, 2026

Related U.S. Application Data

(63) Continuation of application No. 18/514,078, filed on Nov. 20, 2023, now Pat. No. 12,485,167, which is a continuation of application No. 17/323,357, filed on May 18, 2021, now Pat. No. 11,857,621.

(51) Int. Cl.

| | |
|---|---|
| ***A61K 39/215*** | (2006.01) |
| ***A61K 9/00*** | (2006.01) |
| ***A61K 39/00*** | (2006.01) |
| ***A61P 31/14*** | (2006.01) |
| ***C07K 14/005*** | (2006.01) |

(52) U.S. Cl.

CPC .......... *A61K 39/215* (2013.01); *A61K 9/0019* (2013.01); *A61P 31/14* (2018.01); *C07K 14/005* (2013.01); *A61K 2039/53* (2013.01); *A61K 2039/54* (2013.01); *A61K 2039/545* (2013.01); *C12N 2770/20022* (2013.01); *C12N 2770/20034* (2013.01); *C12N 2770/20071* (2013.01)

(58) Field of Classification Search

CPC ................ A61K 39/215; A61K 9/0019; A61K 2039/53; A61K 2039/54; A61K 2039/545; A61P 31/14; C07K 14/005; C12N 2770/20022; C12N 2770/20034; C12N 2770/20071

See application file for complete search history.

(56) References Cited

U.S. PATENT DOCUMENTS

| | | | | |
|---|---|---|---|---|
| 11,857,621 | B2 * | 1/2024 | Almansour .......... | C07K 14/005 |
| 12,485,167 | B2 * | 12/2025 | Almansour .......... | A61K 9/0019 |

FOREIGN PATENT DOCUMENTS

| | | | |
|---|---|---|---|
| CN | 110951756 | A | 4/2020 |
| CN | 111606981 | A | 9/2020 |
| CN | 111671890 | A | 9/2020 |
| RU | 2 720 614 | C1 | 5/2020 |

OTHER PUBLICATIONS

Yu. Science. Aug. 14, 2020;369(6505);806-811. (Year: 2020).*

GenBank Accession No. MW560963.1 (Mar. 21, 2021). (Year: 2021).*

PcDNA3.1+ Mammalian Expression Vector. Thermo Fisher. https://www.thermofisher.com/order/catalog/product/V79020. 6-page printout. Accessed Jan. 11, 2023 . . . (Year: 2023).*

Yu, et al. ; DNA vaccine protection against SARS-CoV-2 in rhesus macaques ; Science 369 ; pp. 806-811 ; Aug. 14, 2020 ; 8 Pages.

Smith, et al. ; Immunogenicity of a DNA vaccine candidate for COVID-19 ; Nature Communications 2020 ; 13 Pages.

Hayashi, et al. ; Preclinical study of DNA vaccines targeting SARS-CoV-2 ; bio Rxiv reprint ; Oct. 21, 2020 ; 33 Pages.

Seo, et al. ; Soluble Spike DNA vaccine provides long-term protective immunity against SAR-CoV-2 in mice and nonhuman primates ; bioRxiv ; Oct. 10, 2020 ; 31 Pages.

Routhu, et al. ; Modified Vaccinia Ankara Based SARS-CoV-2 Vaccine Expressing Full-Length Spike Induces Strong Neutralizing Antibody Response ; bioRxiv ; Jun. 27, 2020 ; 19 Pages.

Almansour, et al ; Immunogenicity of Multiple Doses of pDNA Vaccines against SARS-CoV-2 ; Pharmaceuticals 2021, 14 ; 9 Pages.

Sharp PM, Li WH. The codon Adaptation Index—a measure of directional synonymous codon usage bias, and its potential applications. Nucleic Acids Res. Feb. 11, 1987; 15(3): 1281-95, p. 1281.

PcDNA3.1 + Mammalian Expression Vector. Thermo Fisher. https://www.thermofisher.com/order/catalog/producW79020. 6-page printout. Accessed Jan. 11, 2023.

MW 560963.1 Alignment with SEQ ID No. 1. Nucleotide BLAST. Accessed Jan. 11, 2023.

PcDNA3.1 + Mammalian Expression Vector. Mammalian Expression Vector. Thermo Fisher. https://www.thermofisher.com/order/catalog/producW79020. 6-page printout. Accessed Jan. 11, 2023. (Year: 2023).

Yu, et al. Science. Aug. 14, 2020;369(6505):806-811. doi: 10.1126/science.abc6284. Epub May 20, 2020. PM ID: 32434945. (Year: 2020).

* cited by examiner

*Primary Examiner* — Michael Allen
*Assistant Examiner* — Jeffrey Mark Sifford
(74) *Attorney, Agent, or Firm* — Oblon, McClelland, Maier & Neustadt, L.L.P.

(57) ABSTRACT

A pDNA-based vaccine against SARS-CoV-2 and methods for preventing or treating COVID-19 using it.

11 Claims, 12 Drawing Sheets

Specification includes a Sequence Listing.

Fig. 3A

| Groups | Doses | Vaccines |
|---|---|---|
| 1 | Three | S.opt.FL pDNA |
| 2 | Four | S.opt.FL pDNA |
| 3 | Three | S1.opt pDNA |
| 4 | Four | S1.opt pDNA |
| 5 | Three | S.opt.FL + S1.opt pDNA |
| 6 | Four | S.opt.FL + S1.opt pDNA |
| 7 | Four | Control |

IMMUNIZATION METHOD AGAINST INFECTION BY SARS-CoV-2

CROSS-REFERENCE TO RELATED APPLICATIONS

The present application is a continuation of U.S. application Ser. No. 18/514,078, now allowed, having a filing date of Nov. 20, 2023 which is a continuation of U.S. application Ser. No. 17/323,357, now U.S. Pat. No. 11,857,621, having a filing date of May 18, 2021.

REFERENCE TO A SEQUENCE LISTING

In accordance with 37 CFR § 1.831-1.835 and 37 CFR § 1.77(b) (5) (ii), the specification makes reference to a Sequence Listing submitted electronically as a .xml file named "559983US_ST26". This .xml file was generated on Nov. 21, 2025 and is 37,072 bytes in size. The entire contents of the Sequence Listing are hereby incorporated by reference.

BACKGROUND OF THE INVENTION

Field of the Invention

The disclosure pertains to the design and production of a stable, engineered plasmid DNA (pDNA) SARS-CoV-2 spike (S) protein vaccine that induces protective humoral and cellular responses against SARS-CoV-2.

Description of Related Art

In the 21st century, three coronaviruses that have evolved an ability to cross the species barrier and infect humans have been identified: severe acute respiratory disease syndrome coronavirus (SARS-CoV), Middle East respiratory syndrome (MERS)-CoV, and, most recently, SARS-CoV-2.

SARS-CoV-2 entry is dependent on its surface glycoprotein, the spike (S) protein, which binds to the angiotensin-converting enzyme 2 (ACE2) receptor on host cells. The spike protein is a trimetric type 1 transmembrane protein with each monomer consisting of a receptor binding subunit (S1) and a membrane-fusion subunit S2. As with all human coronaviruses, the S protein is a primary antigenic determinant responsible for eliciting antibodies that prevent viral entry and fusion with a host cell membrane.

Human immunity against coronaviruses is mediated by the production of neutralizing antibodies at levels that are sufficient to confer protection against reinfection. S protein-specific antibodies are detected 1-2 weeks after either natural infection or vaccination. However, the durability of these antibodies following infection with human coronaviruses varies. For example, S protein antibodies elicited by the endemic alpha or beta coronaviruses wane within 12 months, whereas antibodies elicited after infection with SARS-CoV or MERS-CoV can last between 12 and 36 months.

Recent studies have shown that the magnitude of neutralizing antibody responses against SARS-CoV-2 is dependent on disease severity. However, the persistence of these S protein antibodies and whether they can provide long-lasting immunity has yet to be determined.

Resolving this issue is critical for vaccine development, as insufficient neutralizing antibody levels induced after immunization presents a major hurdle for generating effective immunity.

Current vaccines to SARS-CoV include mRNA-based Pfizer BioNTech and Moderna vaccines both of which use lipid nanoparticles to encapsulate the mRNA payload. For example, the Moderna vaccine contains 1,2-distearoyl-sn-glycero-3-phosphocholine, cholesterol, and polyethylene glycol-lipid and the Pfizer vaccine contains similar lipids. The Pfizer vaccine also incorporates 1-methylpseudouridine to reduce immunogenicity of the mRNA and increase its translation rate. RNA vaccines are often difficult to transport and store and often must be kept frozen or refrigerated. Moreover, such vaccines are fragile and are prone to degradation, therefore, these vaccines are often encapsulated, such as the Pfizer and Moderna vaccines. Lipid components have been associated with anaphylaxis and rare allergic reactions in some recipients of these vaccines.

Adenovirus vector vaccines include Oxford-Astrazeneca (currently Vaxzevria), Sputnik V, Convidicea, and Johnson & Johnson COVID-18 vaccines. The Oxford-AstraZeneca vaccine (ChAdOx1) utilizes an adenovirus vector derived from the chimpanzee, incorporating genetic sequences that instruct cellular machinery to produce the full-length spike protein of SARS-CoV-2. The Convidicea (CanSino Biologics) and Johnson & Johnson one-dose vaccines use Adenovirus 5 (Ad5) and 26 (Ad26), respectively. Adenovirus-based vaccine can lack efficacy in subjects who have pre-existing antibodies to adenoviruses. Further, although rare, there is a possible link with occurrence of blood clot in AstraZeneca vaccine recipients. Most of these cases have occurred in vaccine recipients under the age of 55 and they were mostly women (7 DIC and 18 CVST cases). The link with rare blot clot was observed after the administration of first dose of AstraZeneca vaccine. In April 7th, the UK regulators have restricted the use of AstraZeneca to individuals between the age of 18-30 and these were recommended to use alternative vaccines.

Plasmid or pDNA vaccines may offer several unique advantages. These include a high safety profile, economy and cost-effectiveness compared to other vaccines, and ability to be robustly and rapidly manufactured. For example, biosafety level 3 (BSL-3) facilities are not required for the generation of pDNA vaccines. In addition, a pDNA vaccine is thermally stable over extended period of time and pDNA vaccines are more thermostable than mRNA-based vaccines that require transport and storage at low temperatures. Further, unlike with live attenuated and inactivated vaccine where the whole virus is administered to the body, DNA vaccine utilizes a single gene of interest that is responsible for eliciting immunity against a given virus. Therefore, there is no risk for infection or reversion of the virus upon pDNA vaccine administration. However, prior studies indicated that efficacy of a pDNA vaccine depends on the virus type causing the infection and on how a virus interacts with the immune system.

Consequently, the inventor sought to evaluate whether a pDNA-based vaccine could be designed that would provide a high level of protection against infection by SARS-CoV-2. Their pre-clinical studies evaluated the immunogenicity of representative SARS-CoV-2 pDNA vaccines that targeted full length S protein as well as the S1 subunit of S protein. The side-by-side efficacy of these constructs was determined based on induction of humoral, antibody-medicated responses as well as by production of interferon-γ, which is a cytokine important for innate and adaptive immunity against viral pathogens and an inducer of Class II MHC expression.

BRIEF SUMMARY OF THE INVENTION

The disclosure is directed to design, synthesis, production, and immunological evaluation of pDNA vaccines that induce humoral and cellular immune responses against SARS-CoV-2, the causative agent of COVID-19. The pDNA vaccines target SARS-CoV-2 S protein determinants, are thermostable and do not require encapsulation; their production is highly scalable and they may be produced rapidly and in large quantities. The pDNA vaccines may be conveniently administered intramuscularly without the need for electroporation or use of a gene gun.

Other embodiments of this technology include, but are not limited to the following.

A plasmid DNA that comprises the nucleic acid sequence of SEQ ID NO: 1 or 3 or a fragment thereof, which encodes an immunogenic portion of SARS-CoV-2 S1 protein; or that comprises a nucleic acid sequence at least 99% identical to SEQ ID NO: 1 or 3 or a fragment thereof, which encodes an immunogenic portion of SARS-CoV-2 S1 protein. In a preferred embodiment, the amino acid sequence is selected and modified according to a selected human codon usage, GC content, and other criteria for selection of the modified DNA sequence.

The plasmid DNA typically encodes a protein having the amino acid sequence of SEQ ID NO: 7 or encodes a portion thereof, such as an S1 or S2 segment or other immunogenic segment.

In some embodiments it may encode a protein that is at least 95, 96, 97, 98, 99 or >99% identical to the protein of SEQ ID NO: 7 or an immunogenic segment thereof. Typically the plasmid DNA will comprise one or more enhancements to the DNA sequence as disclosed herein.

In one embodiment, the plasmid DNA encodes a full-length S protein.

In another embodiment, the plasmid DNA encodes an S protein or fragment thereof comprising a receptor binding domain (RBD).

In one embodiment, the plasmid DNA encodes an S protein or fragment thereof that lacks all or part of the S2 domain.

In some embodiments, the plasmid DNA encodes an S protein or fragment thereof that lacks at least one of a fusion peptide (FP), a heptad repeat region 1 (HR1), a heptad repeat region 2 (HR2), a transmembrane domain (TM) or a cytoplasmic domain.

In some embodiments the plasmid DNA encodes an S protein consisting of the S1 protein.

In some embodiments, the plasmid DNA may encode a variant full-length S protein or S1 protein that comprises 1, 2, 3, 4, 5, 6, 7, 8, 9, 10 or more amino acid residue deletions, substitutions, or additions to the amino acid sequence described by SEQ ID NO: 7; or that encodes an S protein or S1 protein that is at least 95, 96, 97, 98, 99 or <100% identical to that of SEQ ID NO: 7. In such embodiments, the plasmid DNA insert encoding S or S1 proteins, variants thereof, or immunogenic fragments thereof typically comprise one, two, three or more enhancements as disclosed herein. Such enhancements include, but are not limited to, differences in number or location of CpG sites, CAI, or GC content.

In further embodiments, the plasmid DNA encodes a number or distribution of CpG sites that differs compared to the CpG sites of the polynucleotide of SEQ ID NO: 1 or 3 (gene inserts) or in a plasmid comprising SEQ ID NOS: 2 or 4 (constructs), and which typically differs from that of a corresponding polynucleotide sequence described by SEQ ID NO: 6 (Wuhan Hu 1).

In some embodiments, the plasmid DNA comprises a number of CpG sites that is fewer or that is greater than the number of CpG sites in the polynucleotide of SEQ ID NO: 1 or 3 or in the plasmid comprising SEQ ID NOS: 2 or 4 and which typically differs from that of a corresponding polynucleotide sequence described by SEQ ID NO: 6 (Wuhan Hu 1).

In other embodiments, the plasmid DNA has a codon adaptation index (CAI) for the nucleic acid encoding the immunogenic portion of the S or S1 protein that ranges from 0.91, 0.92, 0.93, 0.94, 0.95, 0.96, 0.97, 0.98, 0.99, to 1.00 and which typically differs from that of a corresponding polynucleotide sequence described by SEQ ID NO: 6.

In some embodiments, the plasmid DNA has a GC content in the nucleic acid encoding the immunogenic portion of the S or S1 protein ranging from 50, 51, 52, 53, 54, 55, 56, 57, 58, 59 to 60% and which typically differs from that of a corresponding polynucleotide sequence described by SEQ ID NO: 6.

In preferred embodiments, the plasmid DNA comprises an enhancer-promoter of mammalian origin, such as a CMV enhancer-promoter of mammalian origin.

In some embodiments, the plasmid DNA comprises a pcDNA3.1(+) vector.

In one embodiment, the plasmid DNA is S.opt.FL.

In one embodiment, the plasmid DNA is S1.opt.

Another aspect of the invention is directed to a composition comprising the plasmid DNA as disclosed herein and a pharmaceutically acceptable carrier or adjuvant. Preferably, the plasmid DNA is not encapsulated or is lipid-free or polyethylene glycol (PEG)-free.

Another aspect of the disclosure is directed to a method for inducing humoral and/or cellular immunity to infection by SARS-Cov-2 comprising administering the DNA vaccine as disclosed herein to a subject in need thereof. In some embodiments of this method the vaccine is administered as two, three, four or more intramuscular injections at intervals of one to three weeks. Preferably, the pDNA is administered to a human subject, but in some cases, may be administered to an animal susceptible to infection by SARS-CoV-2 or an animal vector or carrier of this virus. The pDNA may be administered to mammals such as simians, dogs, cats, camels, mink, or bats or other animals known to carry or transmit coronaviruses.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings below.

FIG. 3A. Schematic of the C57BL/6 mice immunization with SARS-CoV-2 vaccines. Immunization groups and doses for the plasmid (p)DNA vaccines. All immunizations were received intramuscularly with 100 μg per dose, except the phosphate-buffered saline (PBS) control group.

The highest dilution that gave an optical density (OD) 450 twofold higher than that of the prebleed sera (week 0) was designated as the antibody endpoint titer in the graphs above. Antibody titers were expressed as mean endpoint titers; standard error of the mean (SEM) for each vaccine group with an individual scatter dot plot (n=6). Data were compared by one-way ANOVA followed by Tukey's multiple comparison test. ns: no significant difference. The asterisks refer to the level of significance: ****p<0.0001; ns: no significant difference.

Figure 5A:
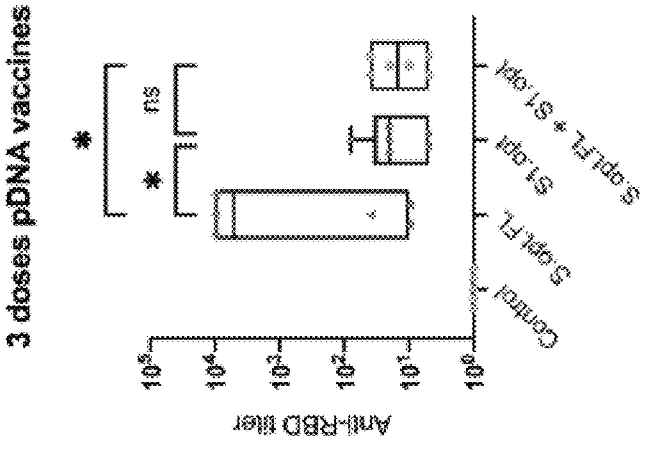

FIG. 5A. Box-and-whisker plot of surrogate virus neutralization test (sVNT). Titer of antireceptor-binding domain (RBD) IgG antibodies from serially diluted mice vaccinated sera taken 2 weeks after the third immunization.

Figure 5B:
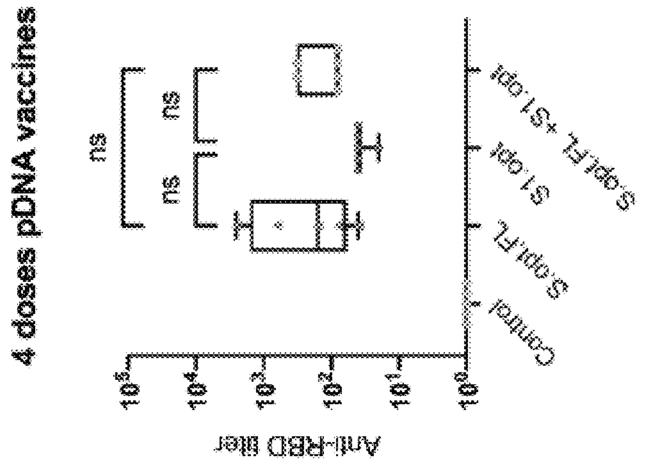

FIG. 5B. Box-and-whisker plot of surrogate virus neutralization test (sVNT). Titer of anti-RBD IgG antibodies from serially diluted mice vaccinated sera taken 2 weeks after the fourth immunization. Cutoff titer was calculated as the serum highest dilution showing a cutoff value >20%. Data were analyzed with one-way ANOVA with Tukey's multiple comparison test. The asterisks refer to the level of significance: *p<0.033; ns: no significant difference.

Figure 6:
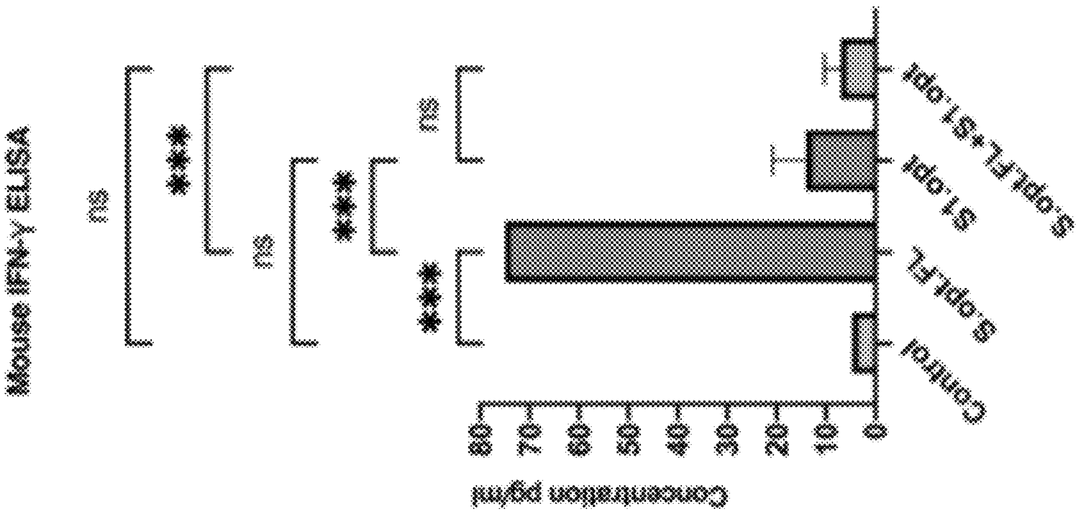

FIG. 6. IFN-γ responses following C57BL/6 mice vaccinations. Comparison of serum IFN-γ levels in each of the vaccine constructs (S.opt.FL, S1.opt, and S.opt.FL+S1.opt) 2 weeks following second immunization in each vaccine construct using pooled mice sera from each group. Endpoint concentration was determined by titers expressed (mean±SD). Data were analyzed with one-way ANOVA with Tukey's multiple comparison test. The asterisks refer to the level of significance: ***p<0.0002; ns: no significant difference.

Figure 7:
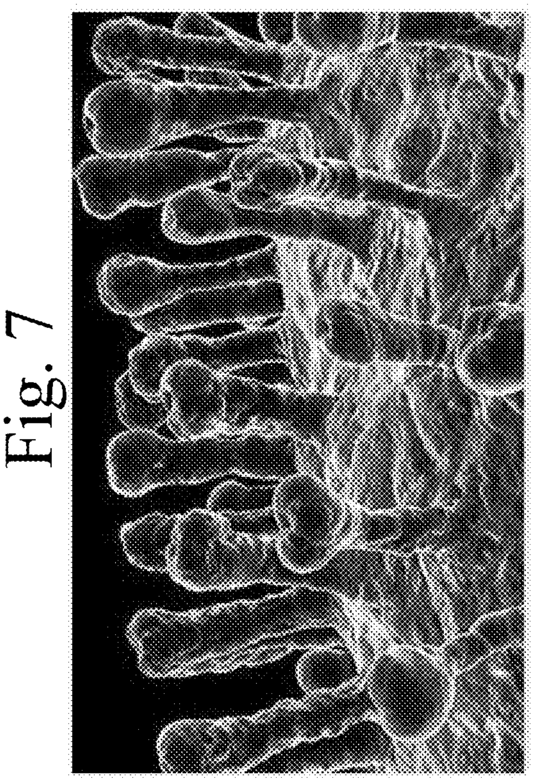

FIG. 7 shows a micrograph of S protein trimers on the surface of SARS-CoV-2.

Figure 8A:
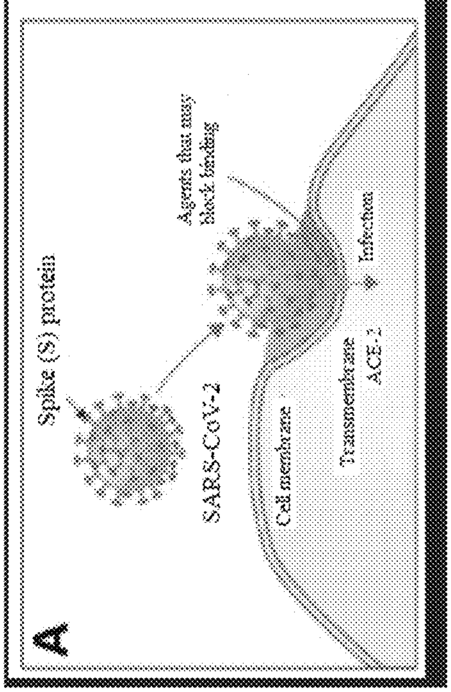
Figure 8B:
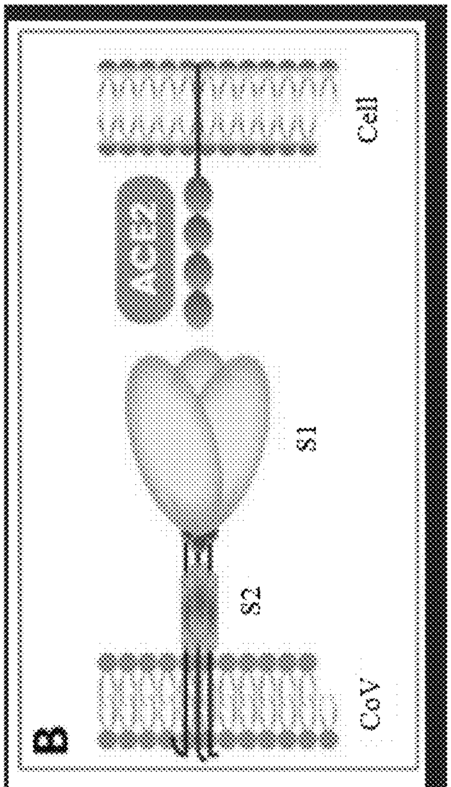

FIGS. 8A and 8B illustrate the role of S protein in viral attachment and invasion.

DETAILED DESCRIPTION OF THE INVENTION

One aspect of the invention is directed to a pDNA or pDNA vaccine that induces protective humoral and/or cellular responses against SARS-CoV-2 S protein epitopes and to methods using the pDNA to prevent or treat SARS-CoV-2 infection. Surprisingly, it has been found that particular modifications to DNA encoding full-length S protein or the S1 subunit of S protein, enhance vaccine efficacy and stability and specific pDNA vectors are disclosed herein that have been demonstrated to induce immune responses targeting SARS-CoV-2.

SARS-CoV-2 Spike (S) protein. The total length of SARS-CoV-2 S is 1273 aa and consists of a signal peptide (amino acids 1-13) located at the N-terminus, the S1 subunit (14-685 residues), and the S2 subunit (686-1273 residues); the last two regions are responsible for receptor binding and membrane fusion, respectively. In the S1 subunit, there is an N-terminal domain (14-305 residues) and a receptor-binding domain (RBD, 319-541 residues); the fusion peptide (FP) (788-806 residues), heptapeptide repeat sequence 1 (HR1) (912-984 residues), HR2 (1163-1213 residues), TM domain (1213-1237 residues), and cytoplasm tail (1237-1273 residues) comprise the S2 subunit. S protein trimers visually form a characteristic bulbous, crown-like halo surrounding the viral particle. Based on the structure of coronavirus S protein monomers, the S1 subunit forms the globular head while S2 subunits forms the stalk region. FIGS. 7 and 8 illustrate S protein and S protein mediated attachment and invasion of a host cell.

S protein polynucleotide or polypeptide variants. In some embodiments the segment of plasmid DNA encoding a segment of S protein, including but not limited to, full-length S protein or the S1 subunit of S protein or an immunogenic segment of S protein, may comprise an polynucleotide sequence that is at least 95, 96, 97, 98, 99 or <100% identical to SEQ ID NO: 1 or 3 or have 1, 2, 3, 4, 5, 6, 7, 8, 9, 10 or more deletions, substitutions, or insertions of nucleotides to a sequence of SEQ ID NO: 1 or 3, and encode a protein that comprises at least one epitope of S protein.

In some embodiments, the plasmid DNA may encode a variant full-length S protein or S1 protein that comprises 1, 2, 3, 4, 5, 6, 7, 8, 9, 10 or more amino acid residue deletions, substitutions, or additions to the amino acid sequence encoded by SEQ ID NOS: 1, 2, 3, or 4 or that encodes an S protein or S1 protein that is at least 95, 96, 97, 98, 99 or <100% identical to that encoded by SEQ ID NOS: 1, 2, 3 or 4.

BLASTN may be used to identify a polynucleotide sequence having at least 70%, 75%, 80%, 85%, 87.5%, 90%, 92.5%, 95%, 97.5%, 98%, 99% or <100% sequence identity to a reference polynucleotide such as a polynucleotide encoding an S protein, antigenic or immunogenic S protein fragment, or S1 subunit. A representative BLASTN setting modified to find highly similar sequences uses an Expect Threshold of 10 and a Wordsize of 28, max matches in query range of 0, match/mismatch scores of 1/−2, and linear gap cost. Low complexity regions may be filtered or masked. Default settings of a Standard Nucleotide BLAST are described by and incorporated by reference to <hypertext transfer protocol secure://blast.ncbi.nlm.nih.gov/Blast.cgi?PROGRAM=blastn&PAGE_TYPE=BlastSearch&LINK_LOC=blasthome> (last accessed Mar. 23, 2021).

BLASTP can be used to identify an amino acid sequence having at least 70%, 75%, 80%, 85%, 87.5%, 90%, 92.5%, 95%, 97.5%, 98%, 99% or <100% sequence identity, or similarity to a reference amino acid, such as an S protein, S1 subunit protein, or antigenic or immunogenic segment of S protein, amino acid sequence, using a similarity matrix such as BLOSUM45, BLOSUM62 or BLOSUM80 where BLO- SUM45 can be used for closely related sequences, BLOSUM62 for midrange sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting that uses an Expect Threshold of 10, a Word Size of 3, BLOSUM 62 as a matrix, and Gap Penalty of 11 (Existence) and 1 (Extension) and a conditional compositional score matrix adjustment. Other default settings for BLASTP are described by and incorporated by reference to the disclosure available at: <hypertext transfer protocol secure://blast.ncbi.nlm.nih.gov/Blast.cgi?PROGRAM=blastp&PAGE_TYPE=BlastSearch&LINK_LOC=blasthome> (last accessed Mar. 23, 2021).

The inventor made several modifications to the SARS-CoV-2 S protein and S1 protein nucleic acid sequences to attain these benefits.

Codon-modification. The genetic code is composed of 64 codons with only 21 amino acid and "stop" assignments. Therefore, degeneracy is inherently designed into translation. Preferential usage of particular codons varies by organism. For example, leucine is specified by 6 distinct codons, some of which are rarely used. By rebalancing codon usage within a reading frame, preferred leucine codons are selected over rarely used codons. However, whether codon-modification will enhance the expression of a recombinant protein is unpredictable and will vary depending on the particular protein and expression system. It also depends on many other factors including vector selection, the number of tRNA copies for a particular codon in a host cell, mRNA stability, protein folding kinetics, protein stability, protein transport, toxicity of the protein within the expression cell environment.

Codon Adaptation Index (CAI) is the most widespread technique for analyzing codon usage bias. As opposed to other measures of codon usage bias, such as the effective number of codons (Nc), which measure deviation from a uniform bias (null hypothesis), CAI measures the deviation of a given protein coding gene sequence with respect to a reference set of genes. CAI is used as a quantitative method of predicting the level of expression of a gene based on its codon sequence; see Sharp, Paul M. & Li, Wen-Hsiung, *The codon adaptation index—a measure of directional synonymous codon usage bias, and its potential applications*, NUCLEIC ACIDS RESEARCH, 1987, 15 (3): 1281-1295 (incorporated by reference). Software suitable for optimizing codon usage is known and may be used to optimize codon usage in a pDNA construct or a segment thereof, such as an immunogenic portion of the S protein of SARS-CoV-2; see Optimizer available at <hypertext transfer protocol://genomes._urv.cat/OPTIMIZER/> (last accessed Mar. 17, 2021). Codon usage frequencies for various organisms are known and are also incorporated by reference to hypertext transfer protocol://genomes.urv.cat/OPTIMIZER/CU_human_nature.html or to the Codon Usage Database at worldwide web.kazusa.or.jp/codon/ (last accessed Mar. 17, 2021).

A pDNA construct or its elements as described herein may have a CAI ranging from 0.8, 0.90, 0.91, 0.92, 0.93, 0.94, 0.95, 0.96, 0.97, 0.98, 0.99, 1.0, preferably about 0.94. These CAI percentages are considered favorable in terms of level of gene expression from the pDNA.

In some embodiments, the techniques described above are used to design the polynucleotide sequence of the pDNA or pDNA encoding S protein determinants.

GC content. In molecular biology and genetics, GC-content (or guanine-cytosine content) is the percentage of nitrogenous bases in a DNA or RNA molecule that are either guanine (G) or cytosine (C). This measure indicates the proportion of G and C bases out of an implied four total bases, also including adenine and thymine in DNA and adenine and uracil in RNA. GC-content may be given for a certain fragment of DNA or RNA or for an entire genome. When it refers to a fragment, it may denote the GC-content of an individual gene or section of a gene (domain), a group of genes or gene clusters, a non-coding region, or a synthetic oligonucleotide such as a primer. While high GC content may stabilize a DNA construct, its effects on uptake of a pDNA vaccine, structural effects on transcribed mRNA, and expression level of a protein expressed by pDNA cannot be accurately predicted. A pDNA construct as described herein may have a GC content ranging from about 30 to 70%, for example, about 50, 51, 52, 53, 54, 55, 56, 57, 58, 59 or 60, preferably about 55-56%.

CpG dinucleotide content. The CpG sites or CG sites are regions of DNA where a cytosine nucleotide is followed by a guanine nucleotide in the linear sequence of bases along its 5'→3' direction. CpG sites occur with high frequency in genomic regions called CpG islands (or CG islands). Nucleic acids containing CpG motifs can activate host innate and acquired immune responses. Further characterization of CpG sequences which may be used in conjunction with the pDNA vaccine disclosed herein are incorporated by reference to H. L. Davis, Dev Biol (Basel) 2000; 104:165-9.

RNA stability/instability motifs (AU-rich elements, ARE). The presence of AU-rich elements in some mammalian mRNAs tends to destabilize those transcripts through the action of cellular proteins that bind these sequences and stimulate poly(A) tail removal. Adenylate-uridylate-rich elements (AU-rich elements; AREs) are found in the 3' untranslated region (UTR) of many messenger RNAs (mRNAs) that code for proto-oncogenes, nuclear transcription factors, and cytokines. AREs are defined as a region with frequent adenine and uridine bases in a mRNA. FIG. 1 describes the modified sequence containing modifications described below.

Cryptic splicing sites can be present at the mRNA level. A cryptic splice site is a mRNA sequence that has the potential for interacting with the spliceosome. Mutations, including splice site mutations, in the underlying DNA or errors during transcription can activate a cryptic splice site in part of the transcript that usually is not spliced.

Premature polyA sites may occur in a sense strand encoding mRNA. These A-rich coding strands result in premature polyadenylation and aberrant mRNA splicing.

Repeat sequences and Secondary mRNA structures such as hairpins, loops, and stems can cause interference with the translation of protein.

In addition to modification of the S protein nucleic acid sequences, the inventor sought and found that particular vectors were suitable for expression of the modified S protein and S1 subunit nucleic acid sequences.

Plasmid vectors. Description pcDNA™ 3.1(+) and pcDNA™ 3.1(−) are commercially available vectors derived from pcDNA 3 and designed for high-level stable and transient expression in mammalian hosts. High-level stable and non-replicative transient expression can be carried out in most mammalian cells. In some embodiments, other vectors may be selected, for example, based on the promoters they contain or on other features contributing to their genetic stability when administered to a subject. Promoters which may be used to express or enhance expression of S protein determinants include SV40, RSV and CMV promoters. Additional modifications to improve expression rates include the insertion of enhancer sequences, synthetic introns, adenovirus tripartite leader (TPL) sequences and modifications to the polyadenylation and transcriptional termination sequences; see Alarcon, J. B., et al., Parasitology, 1999, 42, 343-410 which is incorporated by reference.

Advantageously, it was found that the pDNA vaccine as disclosed herein was thermostable and did not require encapsulation in order to induce protective humoral and cellular responses against SARS-CoV-2./

Carriers, Excipients and Adjuvants. In a preferred embodiment, the pDNA is not encapsulated and it is not necessary to admix it with a polymer, a liposome, or particles (e.g. microparticles or nanoparticles). For example, it is not necessary to form particles of pDNA and cationic polymers such as polyamines (e.g., polyethyleneimine (PEI), polyhistidine, carboxymethylcellulose (CMC), putrescine, spermidine, or spermine), laminar or multilaminar liposomes, or particles of calcium phosphate, or other compositional forms such as an emulsion, a microcapsule, a microsphere, or a nanoparticle Compositions. Pharmaceutical compositions of the present disclosure comprise an effective amount of pDNA formulation disclosed herein, and/or additional agents, dissolved or dispersed in a pharmaceutically acceptable carrier. The phrases "pharmaceutical" or "pharmacologically acceptable" refers to molecular entities and compositions that produce no adverse, allergic or other untoward reaction when administered to an animal, such as, for example, a human. The preparation of a pharmaceutical composition that contains at least one compound or additional active ingredient will be known to those of skill in the art in light of the present disclosure, as exemplified by Remington's Pharmaceutical Sciences, $21^{st}$ edition, 2005, incorporated herein by reference. Moreover, for animal, mammal or human administration, it will be understood that preparations should meet sterility, pyrogenicity, general safety and purity standards as required by FDA Office of Biological Standards.

A composition disclosed herein may comprise different types of carriers depending on whether it is to be administered in solid, liquid or aerosol form, and whether it needs to be sterile for such routes of administration as injection.

It was also found that the pDNA vaccine as disclosed herein could be easily and conveniently administered intramuscularly.

Routes of administration. Preferably, the pDNA compositions disclosed herein are administered intramuscularly. Other modes for pDNA administration include electroporation and gene gun; see Wang, S. et al., DNA immunization, Curr. Protoc. Microbiol., 2013, 31, 18.3.1-18.3.24, incorporated by reference.

Alternatively, the compositions disclosed herein can be administered intravenously, intradermally, transdermally, intrathecally, intraarterially, intraperitoneally, intranasally, intravaginally, intrarectally, topically, subcutaneously, mucosally, in utero, orally, topically, locally, via inhalation (e.g., by aerosol inhalation, dry powder inhalation), by injection, by infusion, by continuous infusion, by localized perfusion bathing target cells directly, via a catheter, via a lavage, in cremes, in lipid compositions (e.g., in liposomes), or by other method or any combination of the forgoing as would be known to one of ordinary skill in the art (see, for example, Remington's Pharmaceutical Sciences, 2003, incorporated herein by reference).

In certain embodiments, a composition herein and/or additional agents is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with edible carrier that can be assimilated.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally.

Solutions of the compositions disclosed herein as free bases or pharmacologically acceptable salts may be prepared in water suitably mixed with a surfactant, such as hydroxypropylcellulose. In some embodiments, agents such as EDTA or EGTA (e.g., Tris-EDTA buffer) are incorporated to prevent degradation of the pDNA by scavenging divalent cations. Other stabilizers including malic acid, ethanol, and Pluronic F-68 are known in the art and are incorporated by reference to Y. Zeng, et al., Journal of Pharmaceutical Sciences, March 2011, 100, 904-914.

Dispersions of the pDNA may be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety, and purity standards as required by FDA Office of Biologics standards.

Sterile injectable solutions are prepared by incorporating the pDNA compositions in the required amount in the appropriate solvent with various of the other ingredients enumerated above, as required, followed by filter sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

In other embodiments, the compositions may be formulated for administration via various miscellaneous routes, for example, topical (e.g., transdermal) administration, mucosal administration (intranasal, vaginal, etc.) and/or via inhalation.

Pharmaceutical compositions for topical administration may include the compositions formulated for a medicated application such as an ointment, paste, cream or powder. Ointments include all oleaginous, adsorption, emulsion and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and laurocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the pDNA compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in t its entirety). Likewise, the delivery of drugs using intranasal microparticle resins (Takenaga et al., Journal of Controlled Release, 1998, 52, 81-87) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroethylene support matrix is described in U.S. Pat. No. 5,780,045 (specifically incorporated by reference), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Dosage. The actual dosage amount of a composition disclosed herein administered to an animal or human patient can be determined by physical and physiological factors such as body weight or surface area, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.01, 0.02, 0.05, 0.1, 0.2, 0.5 or 1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Dosing Regimen. One skilled in the medical and immunological arts may select an appropriate dosing regimen. To enhance the magnitude of antibody responses against SARS-CoV-2, preferably, a regimen comprises administering three separate doses of pDNA intramuscularly over a four week period, preferably at 2 week intervals (0, 2, 4 weeks). Alternatively, the pDNA vaccine may be administered less frequently, for example, a two dose of the pDNA may be given to healthy individuals intramuscularly.

EXAMPLES

Figure 1A:
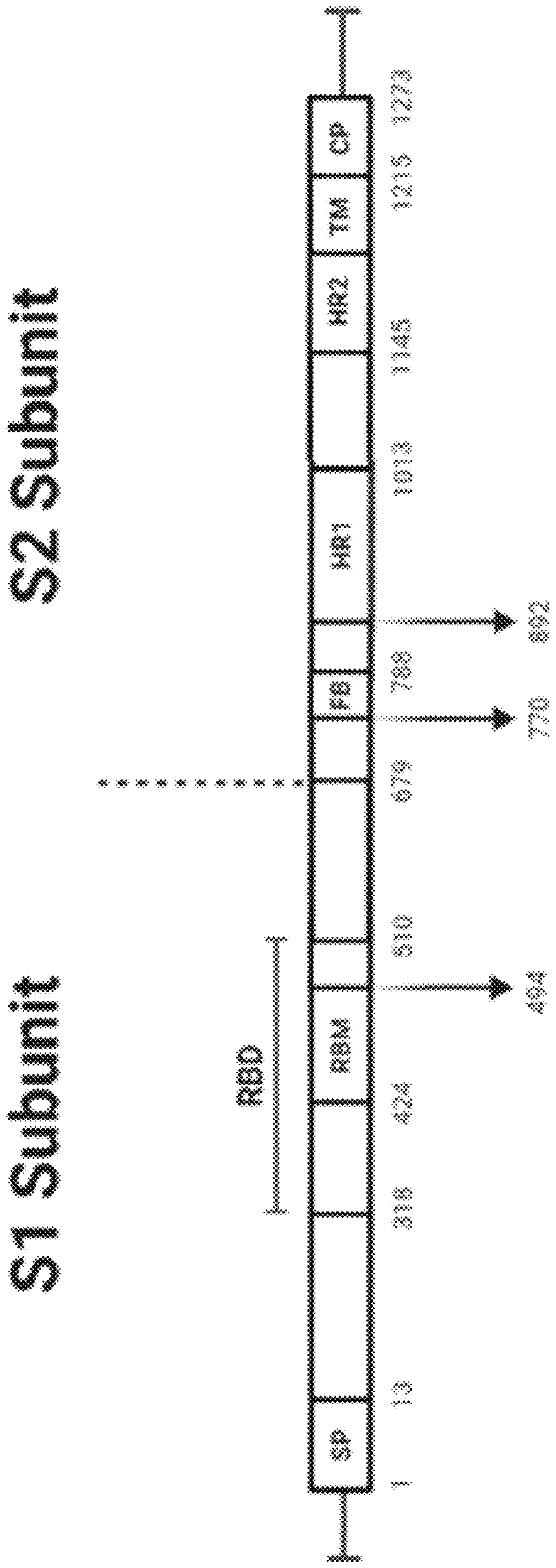
FIG. 1A: Schematic of the severe acute respiratory syndrome coronavirus 2 (SARS-CoV-2) spike (S) glycoprotein. The primary structure of S protein with its S1 and S2 subunits including signal peptide (SP), receptor binding domain (RBS), fusion peptide (FB/FP), heptad repeats (HR1/HR2), transmembrane (TM), and cytoplasmic tail (CP/CT).

Construct Modification and Vaccination Strategy. The S glycoprotein of SARS-CoV is composed of two subunits, S1 and S2. The S1 subunit consists of four domains, namely, the N-terminal domain (NTD), the C-terminal domain (CTD), and subdomains II and I. In addition, the S1 subunit contains the receptor binding domain (RBD), an essential component required for binding to the human (h)ACE2 receptor on the host cell (FIG. 1A).

The S2 subunit consists of the fusion peptide (FP) domain, heptad repeats (HR) 1 and 2, the transmembrane domain (TM), and the cytoplasmic tail (CT). These elements are necessary for the fusion of SARS-CoV-2 with the host cell membrane (FIG. 1A).

Figure 1B:
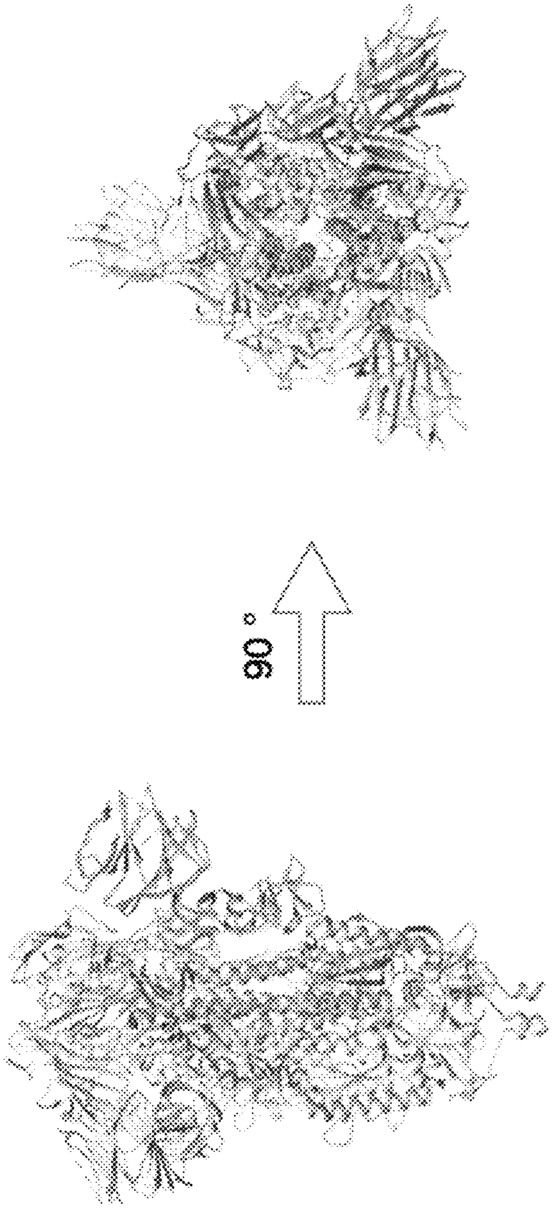
FIG. 1B. Side and top view of the three-dimensional structure of the trimeric spike protein in the perfusion confirmation. Image created from the structure with Protein Data Bank (PDB) identifier VXX6 (incorporated by reference).

The S protein of coronaviruses is a trimeric type I transmembrane, and each monomer consists of S1 and S2 subunits (FIG. 1B).

Figure 2A:
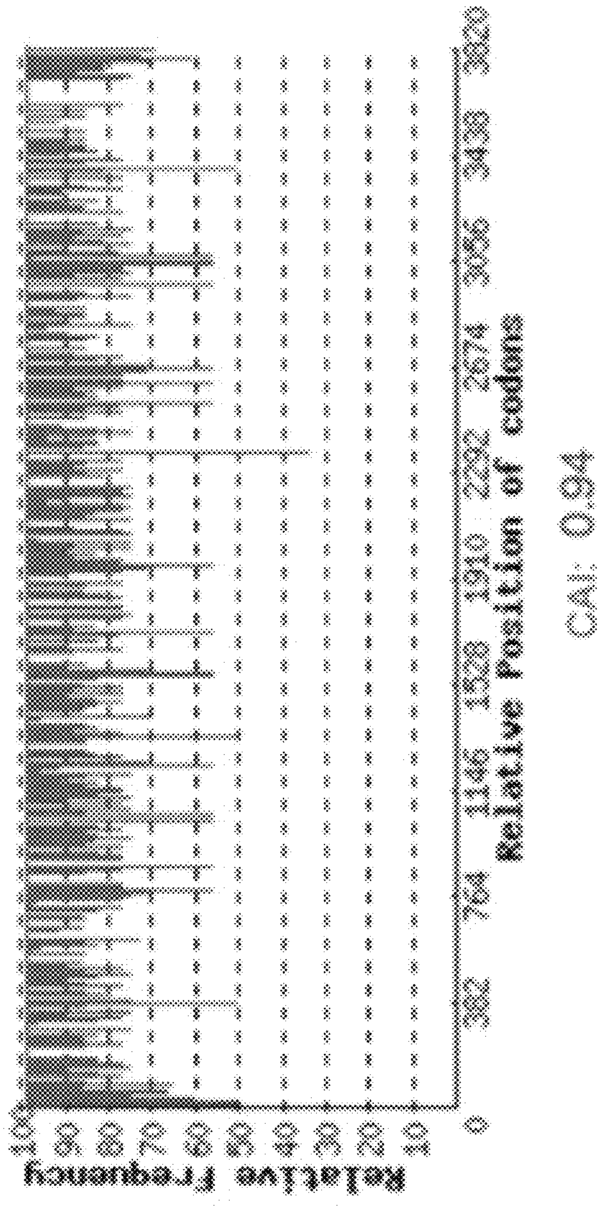
FIG. 2A. Modification of the full-length SARS-CoV-2 spike gene. Distribution of codon usage frequency of the spike (S) protein gene. Codon Adaptation Index (CAI)=0.94.

Two vaccine constructs were tested in this study: pDNA S.opt.FL containing the full-length S gene and pDNA S1.opt including only the globular head, S1 subunit. The codons of S.FL gene were changed to mammalian codon preference (*Homo sapiens*) to enhance the gene expression in mammalian cells (FIG. 2A-C) and were subsequently synthesized and inserted into pcDNA 3.1(+).

Furthermore, the S1.opt was generated from S.FL via mutagenesis study.

Figure 2B:
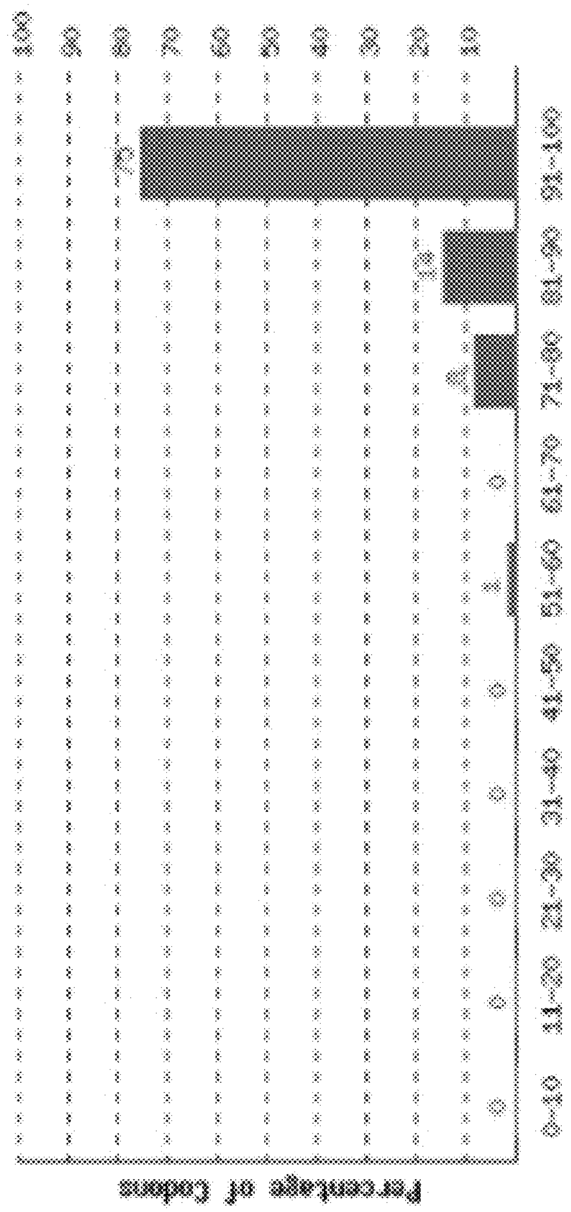
FIG. 2B. Codon distribution percentage computed as codon quality group.
Figure 2C:
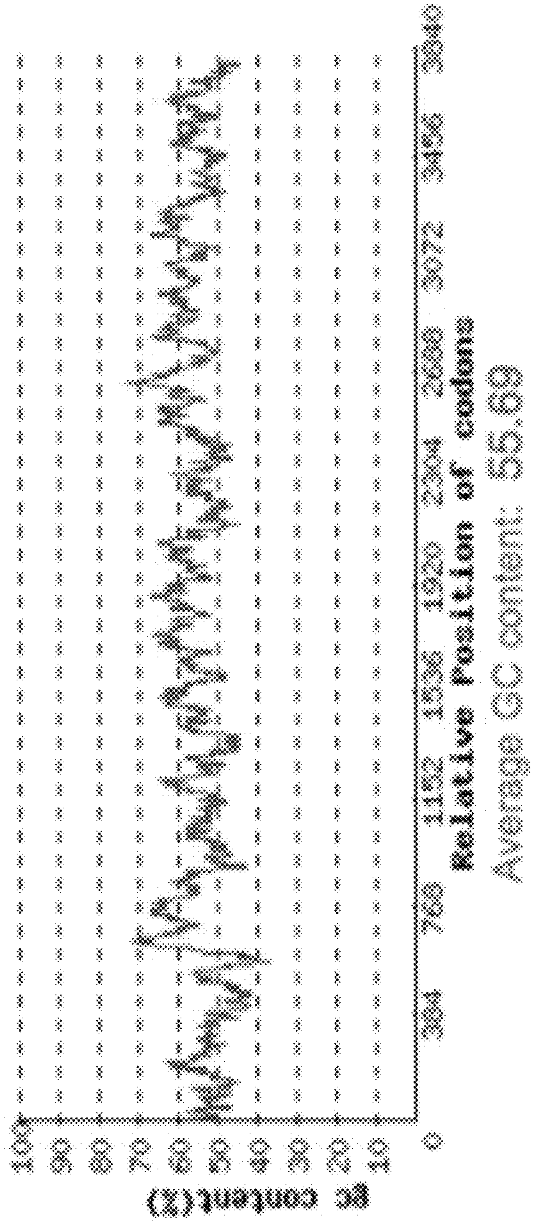
FIG. 2C. GC content adjustment with average equal to 55.69.
Figure 2D:
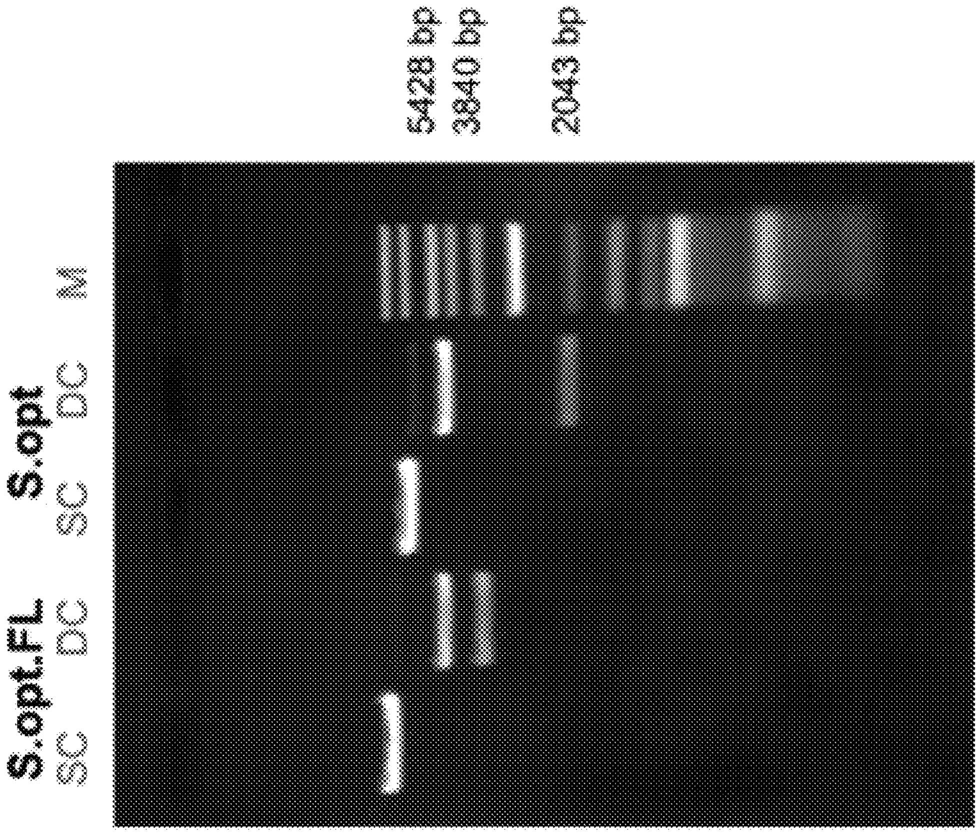
FIG. 2D. Restriction analysis of the S.opt.FL and S1.opt constructs using single-cut (SC) digestion with BamHI and double-cut (DC) digestion with BamHI and NheI.

Both sequences were tested for the correct gene size (FIG. 2B).

Mice were divided into seven groups (n=6 per group); the first group received pDNA S.opt.FL, the second group received pDNA S1.opt, and the third group receive done dose of pDNA S.opt.FL followed by two doses of pDNA S1.opt.

These groups each received three doses of vaccine. Group four received pDNA S.opt.FL, group five received pDNA S1.opt, and group six received one dose of pDNA S.opt.FL followed by three doses of pDNA S1.opt; these groups each received four doses of vaccine.

Group seven was the control group and received only phosphate-buffered saline (PBS) (FIG. 3A). A mouse from the control group died prior to first immunization and another mouse from group 4 died after first immunization.

Immunogenicity in Mice: Production of Binding Antibodies. All C57BL/6 mice were vaccinated intramuscularly (IM) at 6-8 weeks of age with the pDNA vaccines or with the PBS control; blood was collected at 2 week intervals.

Figure 3B:
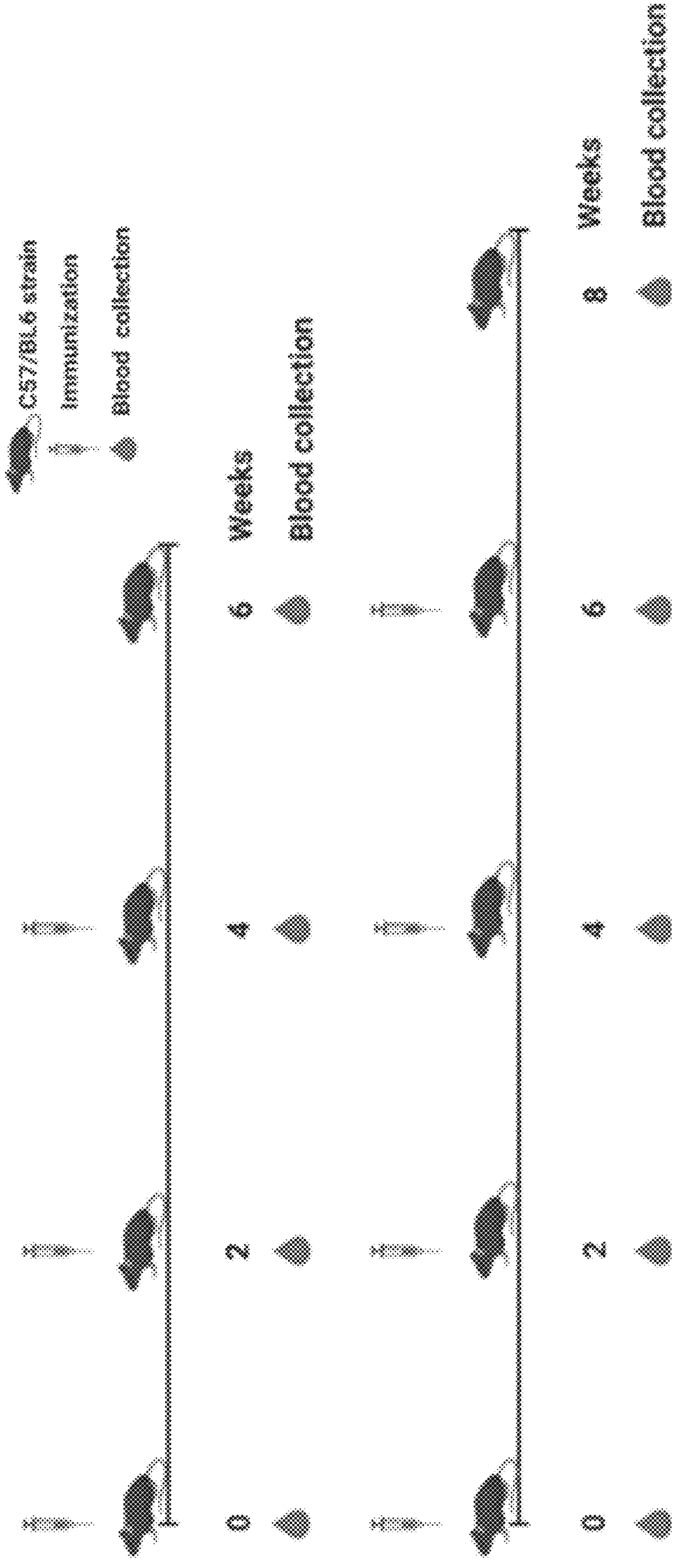
FIG. 3B. The bleeding and immunization regime for the C57BL/6 mice.

Total immunoglobulin G (IgG) antibodies against the S protein were measured in serum samples collected 2 weeks after the last immunization (FIG. 3B).

Figure 4A:
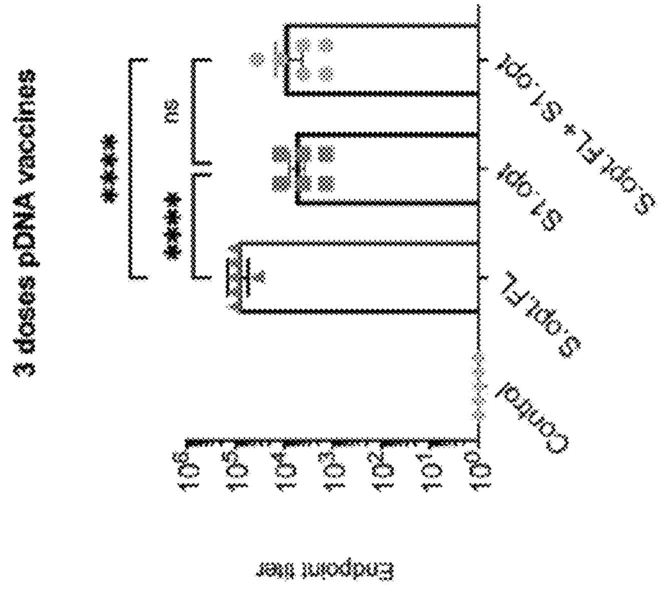
FIG. 4A. Serum endpoint immunoglobulin G (IgG) ELISA titers against autologous full-length spike (S) protein. Total IgG S antibodies were measured in mice sera 2 weeks after the third immunization. Serum starting concentration was 1:50.
Figure 4B:
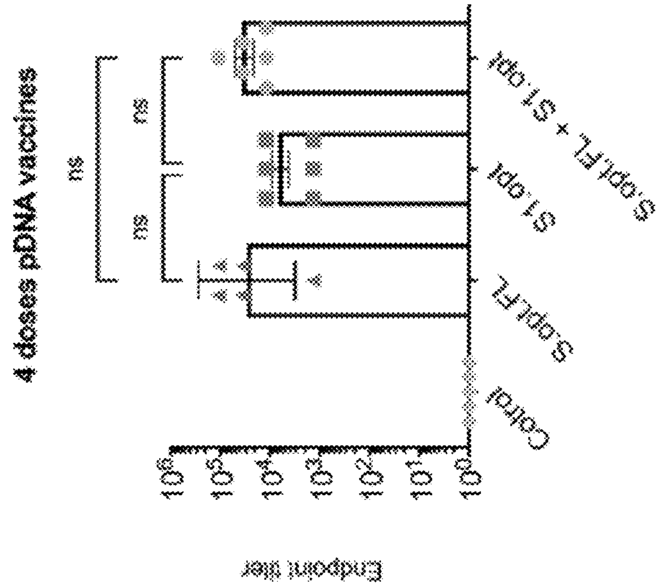
FIG. 4B. Serum endpoint immunoglobulin G (IgG) ELISA titers against autologous full-length spike (S) protein. Total IgG S antibodies were measured in mice sera 2 weeks after the fourth immunization.

The results indicated that sera from all groups of immunized mice, except the PBS control group, contained detectable levels of binding antibodies at weeks 6 and 8 (FIGS. 4A, 4B).

Comparisons among vaccine groups further revealed that mice vaccinated with S.opt.FL pDNA vaccine (groups 1 and 4) generated the highest levels of binding antibodies, with three and four doses of vaccine eliciting equivalent antibody responses (FIGS. 4A,4B).

Mouse groups immunized with the pDNA S1.opt vaccine produced the lowest levels of antibody responses, while the heterologous vaccine produced a moderate immune response (FIG. 4A,4B).

Immunogenicity in Mice: Production of Neutralizing Antibodies. To assess the immunological efficacy of the two pDNA vaccines, a surrogate virus-neutralizing assay was performed. This technique is based on the fact that neutralizing antibodies can block the interaction between the SARS-CoV-2 RBD and the ACE2 receptor.

Neutralization assay results revealed that mice who received three immunization doses with pDNA S.opt.FL produced higher levels of neutralizing antibodies than mice vaccinated with three doses of pDNA S1.opt (FIG. 5A).

Mice immunized with S.opt.FL at weeks 6 and 8 produced similar levels of neutralizing antibodies. It was also found that an additional dose enhanced the levels of neutralizing antibodies; that is, mice who received S.opt.FL priming, followed by the three S1.opt booster doses, had higher antibody responses than those who received only two S1.opt booster doses (FIGS. 5A, 5B).

Interestingly, mice immunized with four doses of S1.opt produced comparable levels of neutralizing antibody responses to immunization with three doses (FIGS. 5A, 5B).

Immunogenicity in Mice: Production of IFN-γ. Recent studies highlighted the role of cell-mediated responses in controlling COVID-19. We, therefore, measured the serum levels of IFN- in mice immunized with our vaccine constructs, as an indicator of innate immunity/cellular immunity.

It was found that consistent with the antibody data, mice immunized with S.opt.FL pDNA vaccine produced significantly higher serum levels of IFN-, relative to the other experimental vaccine groups (FIG. 6).

The pDNA platform is as an attractive strategy for vaccine development during pandemics. This technology is simple and highly scalable. Furthermore, unlike mRNA vaccines that are fragile and require encapsulation to protect from degradation, pDNA vaccines are thermally stable, which is particularly beneficial during vaccine shipment and storage.

Limited data are available on the effect that multiple vaccine doses can have on eliciting potent neutralizing antibodies. The pDNA vaccines designed and produced by the inventor encode the full-length SARS-CoV-2 S gene and S1 as the antigens of interest.

In addition, combining multiple gene inserts in a plasmid vector may interfere with expression of the proteins encoded by these gene inserts; hence, we tested combined administration of the different constructs (S.opt.FL and S1.opt genes) at different doses.

Previous studies on pDNA vaccines against other viral pathogens determined that the optimal dosage required for effective immunity is dependent on the antigen/virus type and how these interact with the immune system. For example, one to two doses of pDNA vaccine are sufficient to produce effective neutralizing antibodies for influenza viruses; however, three to four doses are needed to elicit a sufficient protective immune response in HIV [17].

Neutralizing antibodies against SARS-CoV-2 target the spike RBD known to bind to ACE2 of host cell, thereby blocking viral entry. However, the number of pDNA vaccine doses needed to elicit optimal neutralizing antibody responses to SARS-CoV-2 remains unexplored. The inventor considered that multiple doses of a SARS-CoV-2 pDNA vaccine would be needed to generate an effective SARS-CoV-2 antibody-mediated immune response. Therefore, both a three and four dose regimen of each SARS-CoV-2 pDNA vaccine was used to determine which of these could elicit the most potent neutralizing antibody response.

As shown herein, it was found that three doses of pDNA S.opt.FL vaccine induced the highest levels of neutralizing antibodies, with no added antibody production conferred by the fourth vaccine dose.

In addition, the full-length S protein elicited the most potent immune response, as compared to the pDNA S1.opt vaccine or the S.opt.FL with an S1.opt booster, suggesting that multiple doses of full-length S are needed to elicit high-level immune responses. The inventor consider that non-RBD epitopes may have greater surface accessibility and thus be more immunogenic than some RBD epitopes. Consistent with this observation, mice vaccinated with S.opt.FL elicited higher IFN- production than mice vaccinated with the S1.opt or the combined vaccine. This result is also consistent with the identification of epitopes outside of the S1 domain; see Zheng, et al., Cell Mol. Immunol, 2020 17, 536-538.

The data described herein was obtained following the procedures described below.

Ethics Statement This preclinical study was registered under the Animal Study Registry 10.17590/asr.0000212. Animal protocols were approved by the Institutional Review Board (IRB NO-2020-333-IRMC) at Imam Abdulrahman Bin Faisal University (IAU), and experiments were done in compliance with the institution guidelines.

pDNA Vaccine Constructs. Polynucleotide constructs encoding the full-length S protein (3840 bp) (YP_009724390.1) or its S1 subunit was codon-modified for *Homo sapiens.*

SEQ ID NO: 1 describes the DNA sequence of the gene insert of S.opt.FL which is designated Almansour-I.

SEQ ID NO: 2 describes the DNA sequence of the S.opt.FL construct.

SEQ ID NO: 3 describes the DNA sequence of the gene insert of S1.opt

SEQ ID NO: 4 describes the DNA sequence of the S1.opt construct which is designated Almansour-II.

SEQ ID NO: 5 describes a Kozac sequence.

SEQ ID NO: 6 describes a native DNA sequence encoding SARS CoV-2 Spike protein. This sequence as well as the amino acid sequence it encodes and other information are described by, and incorporated by reference to, NCBI Reference Sequence: NC_045512.2 and to <hypertext transfer protocol secure://www.ncbi.nlm.nih.gov/nuccore/NC_045512.2?reportgenbank&from=21563&to=25384> (last accessed May 3, 2021).

SEQ ID NO: 7 describes an amino acid sequence translated from the DNA sequence of SEQ ID NO: 6.

Other modifications that were made include changes to GC % content, mRNA secondary structure, cryptic splicing sites, premature polyA sites, internal Chi sites, ribosomal-binding sites, and RNA stability motifs. For example, the entire S.FL sequence was codon-enhanced. To increase translation initiation a Kozac sequence (comprising SEQ ID NO: 5) was added downstream of the NheI restriction site in the constructs. A Shine-Dalgarno sequence is not required for eukaryotic expression but may be incorporated for use in prokaryotic expression systems.

The designed sequences were chemically synthesized and BamHI and NheI sequences were incorporated upstream and downstream of the S.opt.FL sequence, respectively. The S.opt.FL sequence was inserted into pcDNA3.1(+) and cloned to further increase the efficiency of translation in eukaryotes. The S1.opt sequence was synthesized by mutagenesis from the template S.opt.FL. A Kozac sequence was added upstream of the coding sequence: (GCCACC SEQ ID NO: 5.

The S.opt.FL was de novo synthesized (GenScript, Piscataway, NJ, USA), and NheI and BamHI restriction sites were incorporated up- and downstream, respectively, of the coding sequence.

The S.opt.FL insert was individually cloned into pcDNA 3.1(+).

The nucleotide sequence of the S.opt.FL construct was confirmed by sequencing. The S1.opt construct (2043 bp) was synthesized by mutagenesis using the synthesized S.opt.FL as a template.

Briefly, a mutagenesis oligo was synthesized and the S.opt.FL_pcDNA 3.1(+) was amplified by PCR using the mutagenesis oligo.

The mutagenesis construct was linearized by NheI and BamHI and subsequently ligated.

The construct was transformed into competent cells and was incubated overnight in LB media with ampicillin at 37° C.

A colony was picked and verified by colony PCR and sequencing.

For pDNA vaccine production, each cloned vaccine construct was grown in LB media containing ampicillin and was incubated overnight at 37° C.

A plasmid DNA purification kit (Cat #12163, QIAGEN®) was used to purify each vaccine construct. The purification levels for S.opt.FL and S1.opt, verified at absorbance 260/280, were 1.91 and 1.89, respectively.

Construct lengths were checked by restriction analyses prior to immunization.

Immunizations. C57BL/6 mice, 6-8 weeks of age, were provided by the King Faisal Specialist Hospital and Research Center, Riyadh, Saudi Arabia. These were maintained by the animal house facility at Imam Abdulrahman Bin Faisal University.

Mice were vaccinated intramuscularly (IM) into the tibialis anterior muscle. For each immunization, animals received 100 μg of pDNA in 200 μL of phosphate-buffered saline (PBS), pH 7.4, or the PBS control.

Mice were administered vaccines at multiple sites.

Serum samples were collected prior to the first immunization and 2 weeks after each immunization.

Enzyme-Linked Immunosorbent Assay (ELISA). For ELISAs, 96-well plates (Cat #44-2404-21; Thermo Fisher Scientific, Waltham, MA, USA) were coated with 10 μg/mL of the full-length S antigen (Cat #Z03483-1, Genscript) and incubated overnight at 4° C. Using a 96-well plate washer, plates were washed five times with 300 μL of 1×PBS. For blocking, 200 μL of 5% non-fat dry milk in Tris-buffered saline (Blocker BLOTTO Cat #170-6404; Bio-Rad Laboratories, Hercules, CA, USA) was added to each well, and plates were incubated for 1 h at room temperature. Blocked plates were washed five times with 300 μL of 1×PBS, and 100 μL of serially diluted serum from vaccinated mice was added to each well, followed by incubation for 1 h at room temperature.

After five washes with 300 μL of 1×PBS, 100 μL of goat anti-mouse IgG secondary antibody conjugated to horseradish peroxidase (HRP) (Cat #31430; Invitrogen, Thermo Fisher Scientific) was added to each well, and plates were incubated for 1 h at room temperature. Plates were washed five times with 300 μL of 1×PBS, and 100_L of tetramethylbenzidine (TMB) substrate (Cat #1854050; Thermo Fisher Scientific) was added to all wells, according to the manufacturer's instructions.

Lastly, 100 μL of 2 M sulfuric acid (2M $H_2SO_4$) was added to all wells to stop reactions; optical density (OD) values were read at 450 nm.

Neutralization Assay. The test used to measure antibody neutralization was based on the surrogate virus neutralization test (Cat #L0084; GenScript), a robust assay for testing vaccine efficacy. Briefly, serum samples, as well as positive and negative controls, were serially diluted and incubated with an equal volume (1:1) of diluted HRP-conjugated receptor-binding domain (RBD) a 37° C. for 30 min.

Mixtures were then added to plates coated with ACE2, which were covered and incubated at 37° C. for 15 min. After washing four times with 1× wash solution, 100 μL of TMB was added to each well, and plates were incubated in the dark at room temperature for 20 min. Lastly, 50 μL of stop solution was added to each well, and the absorbance was read immediately at 450 nm. Percentage neutralization was calculated based on the following formula: (1−sample absorbance/negative control absorbance)×100%, with a cut-off value of >20%.

IFN-gγ Levels of secreted IFN- were measured by ELISA using the mouse IFN- (improved) ELISA Kit (Cat #KMC4021; Invitrogen), according to manufacturer instructions. Briefly, 100 μL of pre-diluted serum samples with standard diluent buffer were added to wells. Samples were incubated at room temperature for 2 h, and plates were washed four times with the provided wash buffer.

Next, 100 μL of streptavidin-HRP solution was added to each well, and plates were incubated at room temperature for 30 min.

After washing four times with wash buffer, 100 μL of stabilized chromogenic substrate was added to each well, and plates were incubated at room temperature for 30 min.

Lastly, 100 μL of stopping solution was added to each well, and plates were read at 450 nm.

The results disclosed above show that immunization with a codon-modified pDNA encoding the full-length or S1 subunit of the SARS-CoV-2 S generated potent and robust binding and neutralizing antibodies, as well as IFN- cytokine responses.

Terminology. Terminology used herein is for the purpose of describing particular embodiments only and is not intended to be limiting of the invention.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for inducing cellular immunity against SARS-COV-2 in a human subject, comprising:

administering, as at least one intramuscular injection, DNA comprising SEQ ID NO: 1, 2, 3 or 4 to the human subject, wherein the DNA encodes an S protein.

2. The method of claim 1, wherein the DNA comprises SEQ ID NO: 2 or SEQ ID NO: 4.

3. The method of claim 1, wherein the DNA comprises (SEQ ID NO: 2).

4. The method of claim 1, wherein the DNA comprises (SEQ ID NO: 4).

5. The method of claim 1, wherein the S protein consists of an S1 protein.

6. The method of claim 1, wherein the DNA is administered in at least two intramuscular injections.

7. The method of claim 6, wherein the DNA is administered at intervals of one to three weeks.

8. The method of claim 1, wherein the DNA is incorporated into a plasmid.

9. The method of claim 1, wherein the DNA comprises SEQ ID NO: 1.

10. The method of claim 1, wherein the DNA comprises a pcDNA3.1(+) vector.

11. The method of claim 6, wherein the DNA is administered as three or more intramuscular injections at intervals of one to three weeks.

* * * * *

SEQUENCE LISTING

```
Sequence total quantity: 7
SEQ ID NO: 1            moltype = DNA  length = 3840
FEATURE                 Location/Qualifiers
misc_feature            1..3840
                        note = Gene insert: S.opt.FL
source                  1..3840
                        mol_type = other DNA
                        organism = synthetic construct
SEQUENCE: 1
gctagcgcca ccatgtttgt ctttctggtc ctgctgcctc tggtgtcatc tcagtgcgtg  60
aacctgacta ctagaactca gctgcccccct gcttatacta attccttcac ccggggcgtg  120
tactatcctg acaaggtgtt tagaagctcc gtgctgcact ctacacagga tctgtttctg  180
ccattcttta gcaacgtgac ctggttccac gccatccacg tgagcggcac caatggcaca  240
aagcggttcg acaatcccgt gctgcctttt aacgatggcg tgtacttcgc ctctaccgag  300
aagagcaaca tcatcagagg ctggatcttt ggcaccacac tggactccaa gacacagtct  360
ctgctgatcg tgaacaatgc caccaacgtg gtcatcaagg tgtgcgagtt ccagttttgt  420
aatgatccct tcctgggcgt gtactatcac aagaacaata agagctggat ggagtccgag  480
tttagagtgt attctagcgc caacaattgc acatttgagt acgtgtccca gcctttcctg  540
atggacctgg agggcaagca gggcaatttc aagaacctga gggagttcgt gtttaagaat  600
atcgatggct acttcaaaat ctacagcaag cacaccccca tcaacctggt gcgcgacctg  660
cctcagggct tcagcgccct ggagcccctg gtggatctgc ctatcggcat caacatcacc  720
cggtttcaga cactgctggc cctgcacaga agctacctga cacccggcga ctcctctagc  780
ggatggaccg caggagctgc cgcctactat gtgggctatc tgcagccccg gaccttcctg  840
ctgaagtaca acgagaatgg caccatcaca gacgcagtgg attgcgccct ggacccccctg  900
agcgagacaa agtgtacact gaagtccttt accgtggaga agggcatcta tcagacatcc  960
aatttcaggg tgcagccaac cgagtctatc gtgcgctttc ctaatatcac aaacctgtgc  1020
ccatttggcg aggtgttcaa cgcaaccagg ttcgccagcg tgtacgcatg gaataggaag  1080
cgcatctcta actgcgtggc cgactatagc gtgctgtaca actccgcctc tttcagcacc  1140
tttaagtgct atggcgtgtc ccccacaaag ctgaatgacc tgtgctttac caacgtgtac  1200
gccgattctt tcgtgatcag gggcgacgag gtgcgccaga tcgcacctgg acagacaggc  1260
aagatcgccg actacaatta taagctgcca gacgatttca ccggctgcgt gatcgcctgg  1320
aacagcaaca atctggattc caaggtcggc ggcaactaca attatctgta ccggctgttt  1380
agaaagagca atctgaagcc cttcgagagg gacatctcta cagaaatcta ccaggccggc  1440
agcacccctt gcaatggcgt ggagggcttt aactgttatt tcccactgca gtcctacggc  1500
ttccagccca caaacggcgt gggctatcag ccttaccgcg tggtggtgct gagctttgag  1560
ctgctgcacg caccagcaac agtgtgcgga cccaagaagt ccaccaatct ggtgaagaac  1620
aagtgcgtga acttcaactt caacggcctg accggcacag gcgtgctgac cgagtccaac  1680
aagaagttcc tgccatttca gcagttcggc agggacatcg cagataccac agacgccgtg  1740
cgcgacccac agaccctgga gatcctggac atcacaccct gctctttcgg cggcgtgagc  1800
gtgatcacac caggcaccaa tacaagcaac caggtggccg tgctgtatca ggacgtgaat  1860
tgtaccgagg tgcctgtggc catccacgcc gatcagctga ccccaacatg gcgggtgtac  1920
agcaccggct ccaacgtgtt ccagacaaga gccggatgcc tgatcggagc agagcacgtg  1980
aacaattcct atgagtgcga catcccaatc ggcgccggca tctgtgcctc ttaccagacc  2040
cagacaaact ctcccagaag agcccggagc gtggcctccc agtctatcat cgcctatacc  2100
atgtccctgg gcgccgagaa cagcgtggcc tactctaaca atagcatcgc catcccaacc  2160
aacttcacaa tctctgtgac cacagagatc ctgcccgtgt ccatgaccaa gacatctgtg  2220
gactgcacaa tgtatatctg tggcgattct accgagtgca gcaacctgct gctgcagtac  2280
ggcagctttt gtacccagct gaatagagcc ctgacaggca tcgccgtgga gcaggataag  2340
aacacacagg aggtgttcgc ccaggtgaag caaatctaca agaccccccc tatcaaggac  2400
tttggcggct tcaatttttc ccagatcctg cctgatccat ccaagccttc taagcggagc  2460
tttatcgagg acctgctgtt caacaaggtg accctggccg atgccggctt catcaagcag  2520
tatggcgatt gcctgggcga catcgcagcc cgggacctga tctgcgccca gaagtttaat  2580
ggcctgaccg tgctgccacc cctgctgaca gatgagatga tcgcacagta cacaagcgcc  2640
ctgctggccg gcaccatcac atccggatgg accttcggcg caggagccgc cctgcagatc  2700
ccctttgcca tgcagatggc ctataggttc aacggcatcg gcgtgaccca gaatgtgctg  2760
tacgagaacc agaagctgat cgccaatcag tttaactccg ccatcggcaa gatccaggac  2820
agcctgtcct ctacagcctc cgccctgggc aagctgcagg atgtggtgaa tcagaacgcc  2880
caggccctga ataccctggt gaagcagctg agcagcaact tcggcgccat ctctagcgtg  2940
ctgaatgaca tcctgagccg gctggacaag gtggaggcag aggtgcagat cgaccggctg  3000
atcacaggca gactgcagtc tctgcagacc tatgtgacac agcagctgat cagggcagca  3060
gagatcaggg ccagcgccaa tctggcagca accaagatgt ccgagtgcgt gctgggccag  3120
tctaagagag tggacttttg tggcaagggc tatcacctga tgtccttccc tcagtctgcc  3180
ccacacggcg tggtgtttct gcacgtgacc tacgtgcccg cccaggagaa gaacttcacc  3240
```

```
acagcccctg ccatctgcca cgatggcaag gcccactttc caagggaggg cgtgttcgtg  3300
tccaacggca cccactggtt tgtgacacag cgcaatttct acgagcccca gatcatcacc  3360
acagacaata ccttcgtgag cggcaactgt gacgtggtca tcggcatcgt gaacaatacc  3420
gtgtatgatc cactgcagcc cgagctggac agctttaagg aggagctgga taagtacttc  3480
aagaatcaca cctcccctga cgtggatctg ggcgacatca gcggcatcaa tgcctccgtg  3540
gtgaacatcc agaaggagat cgaccgcctg aacgaggtgg ccaagaatct gaacgagagc  3600
ctgatcgatc tgcaggagct gggcaagtat gagcagtaca tcaagtggcc ctggtacatc  3660
tggctgggct tcatcgccgg cctgatcgcc atcgtgatgg tgaccatcat gctgtgctgt  3720
atgacatcct gctgttcttg cctgaagggc tgctgtagct gtggctcctg ctgtaagttt  3780
gatgaagatg atagtgaacc cgtgctgaaa ggcgtgaagc tgcattacac ctgaggatcc  3840

SEQ ID NO: 2           moltype = DNA  length = 9231
FEATURE                Location/Qualifiers
misc_feature           1..9231
                       note = S.opt.FL pcDN1 (3.1) construct sequence
source                 1..9231
                       mol_type = other DNA
                       organism = synthetic construct
SEQUENCE: 2
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
gccaccatgt ttgtctttct ggtcctgctg cctctggtgt catctcagtg cgtgaacctg  960
actactagaa ctcagctgcc ccctgcttat actaattcct tcacccgggg cgtgtactat  1020
cctgacaagg tgtttagaag ctccgtgctg cactctacac aggatctgtt tctgccattc  1080
tttagcaacg tgacctggtt ccacgccatc cacgtgagcg gcaccaatgg cacaaagcgg  1140
ttcgacaatc ccgtgctgcc ttttaacgat ggcgtgtact tcgcctctac cgagaagagc  1200
aacatcatca gaggctggat ctttggcacc acactggact ccaagacaca gtctctgctg  1260
atcgtgaaca atgccaccaa cgtggtcatc aaggtgtgcg agttccagtt ttgtaatgat  1320
cccttcctgg gcgtgtacta tcacaagaac aataagagct ggatggagtc cgagtttaga  1380
gtgtattcta gcgccaacaa ttgcacattt gagtacgtgt cccagccttt cctgatggac  1440
ctggagggca agcagggcaa tttcaagaac ctgagggagt tcgtgtttaa gaatatcgat  1500
ggctacttca aaatctacag caagcacacc cccatcaacc tggtgcgcga cctgcctcag  1560
ggcttcagcg ccctggagcc cctggtggat ctgcctatcg gcatcaacat cacccggttt  1620
cagacactgc tggccctgca cagaagctac ctgacacccg gcgactcctc tagcggatgg  1680
accgcaggag ctgccgccta ctatgtgggc tatctgcagc cccggacctt cctgctgaag  1740
tacaacgaga atggcaccat cacagacgca gtggattgcg ccctggaccc cctgagcgag  1800
acaaagtgta cactgaagtc ctttaccgtg gagaagggca tctatcagac atccaatttc  1860
agggtgcagc caaccgagtc tatcgtgcgc tttcctaata tcacaaacct gtgcccattt  1920
ggcgaggtgt tcaacgcaac caggttcgcc agcgtgtacg catggaatag gaagcgcatc  1980
tctaactgcg tggccgacta tagcgtgctg tacaactccg cctctttcag cacctttaag  2040
tgctatggcg tgtcccccac aaagctgaat gacctgtgct ttaccaacgt gtacgccgat  2100
tctttcgtga tcaggggcga cgaggtgcgc cagatcgcac ctggacagac aggcaagatc  2160
gccgactaca attataagct gccagacgat ttcaccggct gcgtgatcgc ctggaacagc  2220
aacaatctgg attccaaggt cggcggcaac tacaattatc tgtaccggct gtttagaaag  2280
agcaatctga agcccttcga gagggacatc tctacagaaa tctaccaggc cggcagcacc  2340
ccttgcaatg gcgtggaggg ctttaactgt tatttcccac tgcagtccta cggcttccag  2400
cccacaaacg gcgtgggcta tcagccttac cgcgtggtgg tgctgagctt tgagctgctg  2460
cacgcaccag caacagtgtg cggacccaag aagtccacca atctggtgaa gaacaagtgc  2520
gtgaacttca acttcaacgg cctgaccggc acaggcgtgc tgaccgagtc caacaagaag  2580
ttcctgccat ttcagcagtt cggcagggac atcgcagata ccacagacgc cgtgcgcgac  2640
ccacagaccc tggagatcct ggacatcaca ccctgctctt tcggcggcgt gagcgtgatc  2700
acaccaggca ccaatacaag caaccaggtg gccgtgctgt atcaggacgt gaattgtacc  2760
gaggtgcctg tggccatcca cgccgatcag ctgaccccaa catggcgggt gtacagcacc  2820
ggctccaacg tgttccagac aagagccgga tgcctgatcg gagcagagca cgtgaacaat  2880
tcctatgagt gcgacatccc aatcggcgcc ggcatctgtg cctcttacca gacccagaca  2940
aactctccca gaagagcccg gagcgtggcc tcccagtcta tcatcgccta taccatgtcc  3000
ctgggcgccg agaacagcgt ggcctactct aacaatagca tcgccatccc aaccaacttc  3060
acaatctctg tgaccacaga gatcctgccc gtgtccatga ccaagacatc tgtggactgc  3120
acaatgtata tctgtggcga ttctaccgag tgcagcaacc tgctgctgca gtacggcagc  3180
ttttgtaccc agctgaatag agccctgaca ggcatcgccg tggagcagga taagaacaca  3240
caggaggtgt tcgcccaggt gaagcaaatc tacaagaccc cccctatcaa ggactttggc  3300
ggcttcaatt tttcccagat cctgcctgat ccatccaagc cttctaagcg gagctttatc  3360
gaggacctgc tgttcaacaa ggtgaccctg gccgatgccg gcttcatcaa gcagtatggc  3420
gattgcctgg gcgacatcgc agcccgggac ctgatctgcg cccagaagtt taatggcctg  3480
accgtgctgc caccccctgct gacagatgag atgatcgcac agtacacaag cgccctgctg  3540
gccggcacca tcacatccgg atggaccttc ggcgcaggag ccgccctgca gatccccttt  3600
```

-continued

```
gccatgcaga tggcctatag gttcaacggc atcggcgtga cccagaatgt gctgtacgag  3660
aaccagaagc tgatcgccaa tcagtttaac tccgccatcg gcaagatcca ggacagcctg  3720
tcctctacag cctccgccct gggcaagctg caggatgtgg tgaatcagaa cgcccaggcc  3780
ctgaataccc tggtgaagca gctgagcagc aacttcggcg ccatctctag cgtgctgaat  3840
gacatcctga gccggctgga caaggtggag gcagaggtgc agatcgaccg gctgatcaca  3900
ggcagactgc agtctctgca gacctatgtg acacagcagc tgatcagggc agcagagatc  3960
agggccagcg ccaatctggc agcaaccaag atgtccgagt gcgtgctggg ccagtctaag  4020
agagtggact tttgtggcaa gggctatcac ctgatgtcct tccctcagtc tgccccacac  4080
ggcgtggtgt ttctgcacgt gacctacgtg cccgcccagg agaagaactt caccacagcc  4140
cctgccatct gccacgatgg caaggcccac tttccaaggg agggcgtgtt cgtgtccaac  4200
ggcacccact ggtttgtgac acagcgcaat ttctacgagc cccagatcat caccacagac  4260
aataccttcg tgagcggcaa ctgtgacgtg gtcatcggca tcgtgaacaa taccgtgtat  4320
gatccactgc agcccgagct ggacagcttt aaggaggagc tggataagta cttcaagaat  4380
cacacctccc ctgacgtgga tctgggcgac atcagcggca tcaatgcctc cgtggtgaac  4440
atccagaagg agatcgaccg cctgaacgag gtggccaaga atctgaacga gagcctgatc  4500
gatctgcagg agctgggcaa gtatgagcag tacatcaagt ggccctggta catctggctg  4560
ggcttcatcg ccggcctgat cgccatcgtg atggtgacca tcatgctgtg ctgtatgaca  4620
tcctgctgtt cttgcctgaa gggctgctgt agctgtggct cctgctgtaa gtttgatgaa  4680
gatgatagtg aacccgtgct gaaaggcgtg aagctgcatt acacctgagg atccactagt  4740
ccagtgtggt ggaattctgc agatatccag cacagtggcg gccgctcgag tctagagggc  4800
ccgtttaaac ccgctgatca gcctcgactg tgccttctag ttgccagcca tctgttgttt  4860
gcccctcccc cgtgccttcc ttgaccctgg aaggtgccac tcccactgtc ctttcctaat  4920
aaaatgagga aattgcatcg cattgtctga gtaggtgtca ttctattctg gggggtgggg  4980
tggggcagga cagcaagggg gaggattggg aagacaatag caggcatgct ggggatgcgg  5040
tgggctctat ggcttctgag gcggaaagaa ccagctgggg ctctaggggg tatccccacg  5100
cgccctgtag cggcgcatta agcgcggcgg gtgtggtggt tacgcgcagc gtgaccgcta  5160
cacttgccag cgccctagcg cccgctcctt tcgctttctt cccttccttt ctcgccacgt  5220
tcgccggctt tccccgtcaa gctctaaatc gggggctccc tttagggttc cgatttagtg  5280
ctttacggca cctcgacccc aaaaaacttg attagggtga tggttcacgt agtgggccat  5340
cgccctgata gacggttttt cgccctttga cgttggagtc cacgttcttt aatagtggac  5400
tcttgttcca aactggaaca acactcaacc ctatctcggt ctattctttt gatttataag  5460
ggattttgcc gatttcggcc tattggttaa aaaatgagct gatttaacaa aaatttaacg  5520
cgaattaatt ctgtggaatg tgtgtcagtt agggtgtgga aagtccccag gctccccagc  5580
aggcagaagt atgcaaagca tgcatctcaa ttagtcagca accaggtgtg gaaagtcccc  5640
aggctcccca gcaggcagaa gtatgcaaag catgcatctc aattagtcag caaccatagt  5700
cccgccccta actccgccca tcccgcccct aactccgccc agttccgccc attctccgcc  5760
ccatggctga ctaatttttt ttatttatgc agaggccgag gccgcctctg cctctgagct  5820
attccagaag tagtgaggag gcttttttgg aggcctaggc ttttgcaaaa agctcccggg  5880
agcttgtata tccattttcg gatctgatca agagacagga tgaggatcgt ttcgcatgat  5940
tgaacaagat ggattgcacg caggttctcc ggccgcttgg gtggagaggc tattcggcta  6000
tgactgggca caacagacaa tcggctgctc tgatgccgcc gtgttccggc tgtcagcgca  6060
ggggcgcccg gttctttttg tcaagaccga cctgtccggt gccctgaatg aactgcagga  6120
cgaggcagcg cggctatcgt ggctggccac gacgggcgtt ccttgcgcag ctgtgctcga  6180
cgttgtcact gaagcgggaa gggactggct gctattgggc gaagtgccgg ggcaggatct  6240
cctgtcatct caccttgctc ctgccgagaa agtatccatc atggctgatg caatgcggcg  6300
gctgcatacg cttgatccgg ctacctgccc attcgaccac caagcgaaac atcgcatcga  6360
gcgagcacgt actcggatgg aagccggtct tgtcgatcag gatgatctgg acgaagagca  6420
tcaggggctc gcgccagccg aactgttcgc caggctcaag gcgcgcatgc ccgacggcga  6480
ggatctcgtc gtgacccatg gcgatgcctg cttgccgaat atcatggtgg aaaatggccg  6540
cttttctgga ttcatcgact gtggccggct gggtgtggcg gaccgctatc aggacatagc  6600
gttggctacc cgtgatattg ctgaagagct tggcggcgaa tgggctgacc gcttcctcgt  6660
gctttacggt atcgccgctc ccgattcgca gcgcatcgcc ttctatcgcc ttcttgacga  6720
gttcttctga gcgggactct ggggttcgaa atgaccgacc aagcgacgcc caacctgcca  6780
tcacgagatt tcgattccac cgccgccttc tatgaaaggt tgggcttcgg aatcgttttc  6840
cgggacgccg gctggatgat cctccagcgc ggggatctca tgctggagtt cttcgcccac  6900
cccaacttgt ttattgcagc ttataatggt tacaaataaa gcaatagcat cacaaatttc  6960
acaaataaag cattttttc actgcattct agttgtggtt tgtccaaact catcaatgta  7020
tcttatcatg tctgtatacc gtcgacctct agctagagct tggcgtaatc atggtcatag  7080
ctgtttcctg tgtgaaattg ttatccgctc acaattccac acaacatacg agccggaagc  7140
ataaagtgta aagcctgggg tgcctaatga gtgagctaac tcacattaat tgcgttgcgc  7200
tcactgcccg ctttccagtc gggaaacctg tcgtgccagc tgcattaatg aatcggccaa  7260
cgcgcgggga gaggcggttt gcgtattggg cgctcttccg cttcctcgct cactgactcg  7320
ctgcgctcgg tcgttcggct gcggcgagcg gtatcagctc actcaaaggc ggtaatacgg  7380
ttatccacag aatcagggga taacgcagga aagaacatgt gagcaaaagg ccagcaaaag  7440
gccaggaacc gtaaaaaggc cgcgttgctg gcgtttttcc ataggctccg cccccctgac  7500
gagcatcaca aaaatcgacg ctcaagtcag aggtggcgaa acccgacagg actataaaga  7560
taccaggcgt ttccccctgg aagctccctc gtgcgctctc ctgttccgac cctgccgctt  7620
accggatacc tgtccgcctt tctcccttcg ggaagcgtgg cgctttctca tagctcacgc  7680
tgtaggtatc tcagttcggt gtaggtcgtt cgctccaagc tgggctgtgt gcacgaaccc  7740
cccgttcagc ccgaccgctg cgccttatcc ggtaactatc gtcttgagtc caacccggta  7800
agacacgact tatcgccact ggcagcagcc actggtaaca ggattagcag agcgaggtat  7860
gtaggcggtg ctacagagtt cttgaagtgg tggcctaact acggctacac tagaagaaca  7920
gtatttggta tctgcgctct gctgaagcca gttaccttcg gaaaaagagt tggtagctct  7980
tgatccggca aacaaaccac cgctggtagc ggtggttttt ttgtttgcaa gcagcagatt  8040
acgcgcagaa aaaaaggatc tcaagaagat cctttgatct tttctacggg gtctgacgct  8100
cagtggaacg aaaactcacg ttaagggatt ttggtcatga gattatcaaa aaggatcttc  8160
acctagatcc ttttaaatta aaaatgaagt tttaaatcaa tctaaagtat atatgagtaa  8220
acttggtctg acagttacca atgcttaatc agtgaggcac ctatctcagc gatctgtcta  8280
tttcgttcat ccatagttgc ctgactcccc gtcgtgtaga taactacgat acgggagggc  8340
```

-continued

```
ttaccatctg gccccagtgc tgcaatgata ccgcgagacc cacgctcacc ggctccagat  8400
ttatcagcaa taaaccagcc agccggaagg gccgagcgca gaagtggtcc tgcaacttta  8460
tccgcctcca tccagtctat taattgttgc cgggaagcta gagtaagtag ttcgccagtt  8520
aatagtttgc gcaacgttgt tgccattgct acaggcatcg tggtgtcacg ctcgtcgttt  8580
ggtatggctt cattcagctc cggttcccaa cgatcaaggc gagttacatg atcccccatg  8640
ttgtgcaaaa aagcggttag ctccttcggt cctccgatcg ttgtcagaag taagttggcc  8700
gcagtgttat cactcatggt tatggcagca ctgcataatt ctcttactgt catgccatcc  8760
gtaagatgct tttctgtgac tggtgagtac tcaaccaagt cattctgaga atagtgtatg  8820
cggcgaccga gttgctcttg cccggcgtca atacgggata ataccgcgcc acatagcaga  8880
actttaaaag tgctcatcat tggaaaacgt tcttcggggc gaaaactctc aaggatctta  8940
ccgctgttga gatccagttc gatgtaaccc actcgtgcac ccaactgatc ttcagcatct  9000
tttactttca ccagcgtttc tgggtgagca aaaacaggaa ggcaaaatgc cgcaaaaaag  9060
ggaataaggg cgacacggaa atgttgaata ctcatactct tcctttttca atattattga  9120
agcatttatc agggttattg tctcatgagc ggatacatat ttgaatgtat ttagaaaaat  9180
aaacaaatag gggttccgcg cacatttccc cgaaaagtgc cacctgacgt c           9231

SEQ ID NO: 3           moltype = DNA  length = 2076
FEATURE                Location/Qualifiers
misc_feature           1..2076
                       note = Gene insert: S1.opt
source                 1..2076
                       mol_type = other DNA
                       organism = synthetic construct
SEQUENCE: 3
gctagcgcca ccatgtttgt ctttctggtc ctgctgcctc tggtgtcatc tcagtgcgtg  60
aacctgacta ctagaactca gctgccccct gcttatacta attccttcac ccggggcgtg  120
tactatcctg acaaggtgtt tagaagctcc gtgctgcact ctacacagga tctgtttctg  180
ccattcttta gcaacgtgac ctggttccac gccatccacg tgagcggcac caatggcaca  240
aagcggttcg acaatcccgt gctgcctttt aacgatggcg tgtacttcgc ctctaccgag  300
aagagcaaca tcatcagagg ctggatcttt ggcaccacac tggactccaa gacacagtct  360
ctgctgatcg tgaacaatgc caccaacgtg gtcatcaagg tgtgcgagtt ccagttttgt  420
aatgatccct tcctgggcgt gtactatcac aagaacaata agagctggat ggagtccgag  480
tttagagtgt attctagcgc caacaattgc acatttgagt acgtgtccca gcctttcctg  540
atggacctgg agggcaagca gggcaatttc aagaacctga gggagttcgt gtttaagaat  600
atcgatggct acttcaaaat ctacagcaag cacaccccca tcaacctggt gcgcgacctg  660
cctcagggct tcagcgccct ggagcccctg gtggatctgc ctatcggcat caacatcacc  720
cggtttcaga cactgctggc cctgcacaga agctacctga cacccggcga ctcctctagc  780
ggatggaccg caggagctgc cgcctactat gtgggctatc tgcagccccg gaccttcctg  840
ctgaagtaca acgagaatgg caccatcaca gacgcagtgg attgcgccct ggaccccctg  900
agcgagacaa agtgtacact gaagtccttt accgtggaga agggcatcta tcagacatcc  960
aatttcaggg tgcagccaac cgagtctatc gtgcgctttc ctaatatcac aaacctgtgc  1020
ccatttggcg aggtgttcaa cgcaaccagg ttcgccagcg tgtacgcatg gaataggaag  1080
cgcatctcta actgcgtggc cgactatagc gtgctgtaca actccgcctc tttcagcacc  1140
tttaagtgct atggcgtgtc ccccacaaag ctgaatgacc tgtgctttac caacgtgtac  1200
gccgattctt tcgtgatcag gggcgacgag gtgcgccaga tcgcacctgg acagacaggc  1260
aagatcgccg actacaatta taagctgcca gacgatttca ccggctgcgt gatcgcctgg  1320
aacagcaaca atctggattc caaggtcggc ggcaactaca attatctgta ccggctgttt  1380
agaaagagca atctgaagcc cttcgagagg gacatctcta cagaaatcta ccaggccggc  1440
agcacccctt gcaatggcgt ggagggcttt aactgttatt tcccactgca gtcctacggc  1500
ttccagccca caaacggcgt gggctatcag ccttaccgcg tggtggtgct gagctttgag  1560
ctgctgcacg caccagcaac agtgtgcgga cccaagaagt ccaccaatct ggtgaagaac  1620
aagtgcgtga acttcaactt caacggcctg accggcacag gcgtgctgac cgagtccaac  1680
aagaagttcc tgccatttca gcagttcggc agggacatcg cagataccac agacgccgtg  1740
cgcgacccac agaccctgga gatcctggac atcacaccct gctctttcgg cggcgtgagc  1800
gtgatcacac caggcaccaa tacaagcaac caggtggccg tgctgtatca ggacgtgaat  1860
tgtaccgagg tgcctgtggc catccacgcc gatcagctga ccccaacatg gcgggtgtac  1920
agcaccggct ccaacgtgtt ccagacaaga gccggatgcc tgatcggagc agagcacgtg  1980
aacaattcct atgagtgcga catcccaatc ggcgccggca tctgtgcctc ttaccagacc  2040
cagacaaact ctcccagaag agcccggtga ggatcc                            2076

SEQ ID NO: 4           moltype = DNA  length = 7467
FEATURE                Location/Qualifiers
misc_feature           1..7467
                       note = S1.opt pcDNA 3.1(+) construct
source                 1..7467
                       mol_type = other DNA
                       organism = synthetic construct
SEQUENCE: 4
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
```

-continued

```
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
gccaccatgt ttgtctttct ggtcctgctg cctctggtgt catctcagtg cgtgaacctg  960
actactagaa ctcagctgcc ccctgcttat actaattcct tcacccgggg cgtgtactat  1020
cctgacaagg tgtttagaag ctccgtgctg cactctacac aggatctgtt tctgccattc  1080
tttagcaacg tgacctggtt ccacgccatc cacgtgagcg gcaccaatgg cacaaagcgg  1140
ttcgacaatc ccgtgctgcc ttttaacgat ggcgtgtact tcgcctctac cgagaagagc  1200
aacatcatca gaggctggat ctttggcacc acactggact ccaagacaca gtctctgctg  1260
atcgtgaaca atgccaccaa cgtggtcatc aaggtgtgcg agttccagtt ttgtaatgat  1320
cccttcctgg gcgtgtacta tcacaagaac aataagagct ggatggagtc cgagtttaga  1380
gtgtattcta gcgccaacaa ttgcacattt gagtacgtgt cccagccttt cctgatggac  1440
ctggagggca agcagggcaa tttcaagaac ctgagggagt tcgtgtttaa gaatatcgat  1500
ggctacttca aaatctacag caagcacacc cccatcaacc tggtgcgcga cctgcctcag  1560
ggcttcagcg ccctggagcc cctggtggat ctgcctatcg gcatcaacat cacccggttt  1620
cagacactgc tggccctgca cagaagctac ctgacacccg gcgactcctc tagcggatgg  1680
accgcaggag ctgccgccta ctatgtgggc tatctgcagc cccggacctt cctgctgaag  1740
tacaacgaga atggcaccat cacagacgca gtggattgcg ccctggaccc cctgagcgag  1800
acaaagtgta cactgaagtc ctttaccgtg gagaagggca tctatcagac atccaatttc  1860
agggtgcagc caaccgagtc tatcgtgcgc tttcctaata tcacaaacct gtgcccattt  1920
ggcgaggtgt tcaacgcaac caggttcgcc agcgtgtacg catggaatag gaagcgcatc  1980
tctaactgcg tggccgacta tagcgtgctg tacaactccg cctctttcag cacctttaag  2040
tgctatggcg tgtcccccac aaagctgaat gacctgtgct ttaccaacgt gtacgccgat  2100
tctttcgtga tcaggggcga cgaggtgcgc cagatcgcac ctggacagac aggcaagatc  2160
gccgactaca attataagct gccagacgat ttcaccggct gcgtgatcgc ctggaacagc  2220
aacaatctgg attccaaggt cggcggcaac tacaattatc tgtaccggct gtttagaaag  2280
agcaatctga agcccttcga gagggacatc tctacagaaa tctaccaggc cggcagcacc  2340
ccttgcaatg gcgtggaggg ctttaactgt tatttcccac tgcagtccta cggcttccag  2400
cccacaaacg gcgtgggcta tcagccttac cgcgtggtgg tgctgagctt tgagctgctg  2460
cacgcaccag caacagtgtg cggacccaag aagtccacca atctggtgaa gaacaagtgc  2520
gtgaacttca acttcaacgg cctgaccggc acaggcgtgc tgaccgagtc caacaagaag  2580
ttcctgccat ttcagcagtt cggcagggac atcgcagata ccacagacgc cgtgcgcgac  2640
ccacagaccc tggagatcct ggacatcaca ccctgctctt tcggcggcgt gagcgtgatc  2700
acaccaggca ccaatacaag caaccaggtg gccgtgctgt atcaggacgt gaattgtacc  2760
gaggtgcctg tggccatcca cgccgatcag ctgaccccaa catggcgggt gtacagcacc  2820
ggctccaacg tgttccagac aagagccgga tgcctgatcg gagcagagca cgtgaacaat  2880
tcctatgagt gcgacatccc aatcggcgcc ggcatctgtg cctcttacca gacccagaca  2940
aactctccca gaagagcccg gtgaggatcc actagtccag tgtggtggaa ttctgcagat  3000
atccagcaca gtggcggccg ctcgagtcta gagggcccgt ttaaacccgc tgatcagcct  3060
cgactgtgcc ttctagttgc cagccatctg ttgtttgccc ctcccccgtg ccttccttga  3120
ccctggaagg tgccactccc actgtccttt cctaataaaa tgaggaaatt gcatcgcatt  3180
gtctgagtag gtgtcattct attctggggg gtggggtggg gcaggacagc aagggggagg  3240
attgggaaga caatagcagg catgctgggg atgcggtggg ctctatggct tctgaggcgg  3300
aaagaaccag ctggggctct agggggtatc cccacgcgcc ctgtagcggc gcattaagcg  3360
cggcgggtgt ggtggttacg cgcagcgtga ccgctacact tgccagcgcc ctagcgcccg  3420
ctcctttcgc tttcttccct tcctttctcg ccacgttcgc cggctttccc cgtcaagctc  3480
taaatcgggg gctcccttta gggttccgat ttagtgcttt acggcacctc gaccccaaaa  3540
aacttgatta gggtgatggt tcacgtagtg ggccatcgcc ctgatagacg gtttttcgcc  3600
ctttgacgtt ggagtccacg ttctttaata gtggactctt gttccaaact ggaacaacac  3660
tcaaccctat ctcggtctat tcttttgatt tataagggat tttgccgatt tcggcctatt  3720
ggttaaaaaa tgagctgatt taacaaaaat ttaacgcgaa ttaattctgt ggaatgtgtg  3780
tcagttaggg tgtggaaagt ccccaggctc cccagcaggc agaagtatgc aaagcatgca  3840
tctcaattag tcagcaacca ggtgtggaaa gtccccaggc tccccagcag gcagaagtat  3900
gcaaagcatg catctcaatt agtcagcaac catagtcccg cccctaactc cgcccatccc  3960
gcccctaact ccgcccagtt ccgcccattc tccgccccat ggctgactaa ttttttttat  4020
ttatgcagag gccgaggccg cctctgcctc tgagctattc cagaagtagt gaggaggctt  4080
ttttggaggc ctaggctttt gcaaaaagct cccgggagct tgtatatcca ttttcggatc  4140
tgatcaagag acaggatgag gatcgtttcg catgattgaa caagatggat tgcacgcagg  4200
ttctccggcc gcttgggtgg agaggctatt cggctatgac tgggcacaac agacaatcgg  4260
ctgctctgat gccgccgtgt tccggctgtc agcgcagggg cgcccggttc tttttgtcaa  4320
gaccgacctg tccggtgccc tgaatgaact gcaggacgag gcagcgcggc tatcgtggct  4380
ggccacgacg ggcgttcctt gcgcagctgt gctcgacgtt gtcactgaag cgggaaggga  4440
ctggctgcta ttgggcgaag tgccggggca ggatctcctg tcatctcacc ttgctcctgc  4500
cgagaaagta tccatcatgg ctgatgcaat gcggcggctg catacgcttg atccggctac  4560
ctgcccattc gaccaccaag cgaaacatcg catcgagcga gcacgtactc ggatggaagc  4620
cggtcttgtc gatcaggatg atctggacga agagcatcag gggctcgcgc cagccgaact  4680
gttcgccagg ctcaaggcgc gcatgcccga cggcgaggat ctcgtcgtga cccatggcga  4740
tgcctgcttg ccgaatatca tggtggaaaa tggccgcttt tctggattca tcgactgtgg  4800
ccggctgggt gtggcggacc gctatcagga catagcgttg gctacccgtg atattgctga  4860
agagcttggc ggcgaatggg ctgaccgctt cctcgtgctt tacggtatcg ccgctcccga  4920
ttcgcagcgc atcgccttct atcgccttct tgacgagttc ttctgagcgg gactctgggg  4980
ttcgaaatga ccgaccaagc gacgcccaac ctgccatcac gagatttcga ttccaccgcc  5040
gccttctatg aaaggttggg cttcggaatc gttttccggg acgccggctg gatgatcctc  5100
cagcgcgggg atctcatgct ggagttcttc gcccacccca acttgtttat tgcagcttat  5160
aatggttaca aataaagcaa tagcatcaca aatttcacaa ataaagcatt tttttcactg  5220
cattctagtt gtggtttgtc caaactcatc aatgtatctt atcatgtctg tataccgtcg  5280
acctctagct agagcttggc gtaatcatgg tcatagctgt ttcctgtgtg aaattgttat  5340
ccgctcacaa ttccacacaa catacgagcc ggaagcataa agtgtaaagc ctggggtgcc  5400
```

-continued

```
taatgagtga gctaactcac attaattgcg ttgcgctcac tgcccgcttt ccagtcggga  5460
aacctgtcgt gccagctgca ttaatgaatc ggccaacgcg cggggagagg cggtttgcgt  5520
attgggcgct cttccgcttc ctcgctcact gactcgctgc gctcggtcgt tcggctgcgg  5580
cgagcggtat cagctcactc aaaggcggta atacggttat ccacagaatc aggggataac  5640
gcaggaaaga acatgtgagc aaaaggccag caaaaggcca ggaaccgtaa aaaggccgcg  5700
ttgctggcgt ttttccatag gctccgcccc cctgacgagc atcacaaaaa tcgacgctca  5760
agtcagaggt ggcgaaaccc gacaggacta taaagatacc aggcgtttcc ccctggaagc  5820
tccctcgtgc gctctcctgt tccgaccctg ccgcttaccg gatacctgtc cgcctttctc  5880
ccttcgggaa gcgtggcgct ttctcatagc tcacgctgta ggtatctcag ttcggtgtag  5940
gtcgttcgct ccaagctggg ctgtgtgcac gaaccccccg ttcagcccga ccgctgcgcc  6000
ttatccggta actatcgtct tgagtccaac ccggtaagac acgacttatc gccactggca  6060
gcagccactg gtaacaggat tagcagagcg aggtatgtag gcggtgctac agagttcttg  6120
aagtggtggc ctaactacgg ctacactaga agaacagtat ttggtatctg cgctctgctg  6180
aagccagtta ccttcggaaa aagagttggt agctcttgat ccggcaaaca aaccaccgct  6240
ggtagcggtg gtttttttgt ttgcaagcag cagattacgc gcagaaaaaa aggatctcaa  6300
gaagatcctt tgatcttttc tacggggtct gacgctcagt ggaacgaaaa ctcacgttaa  6360
gggattttgg tcatgagatt atcaaaaagg atcttcacct agatcctttt aaattaaaaa  6420
tgaagtttta aatcaatcta aagtatatat gagtaaactt ggtctgacag ttaccaatgc  6480
ttaatcagtg aggcacctat ctcagcgatc tgtctatttc gttcatccat agttgcctga  6540
ctccccgtcg tgtagataac tacgatacgg gagggcttac catctggccc cagtgctgca  6600
atgataccgc gagacccacg ctcaccggct ccagatttat cagcaataaa ccagccagcc  6660
ggaagggccg agcgcagaag tggtcctgca actttatccg cctccatcca gtctattaat  6720
tgttgccggg aagctagagt aagtagttcg ccagttaata gtttgcgcaa cgttgttgcc  6780
attgctacag gcatcgtggt gtcacgctcg tcgtttggta tggcttcatt cagctccggt  6840
tcccaacgat caaggcgagt tacatgatcc cccatgttgt gcaaaaaagc ggttagctcc  6900
ttcggtcctc cgatcgttgt cagaagtaag ttggccgcag tgttatcact catggttatg  6960
gcagcactgc ataattctct tactgtcatg ccatccgtaa gatgcttttc tgtgactggt  7020
gagtactcaa ccaagtcatt ctgagaatag tgtatgcggc gaccgagttg ctcttgcccg  7080
gcgtcaatac gggataatac cgcgccacat agcagaactt taaaagtgct catcattgga  7140
aaacgttctt cggggcgaaa actctcaagg atcttaccgc tgttgagatc cagttcgatg  7200
taacccactc gtgcacccaa ctgatcttca gcatctttta ctttcaccag cgtttctggg  7260
tgagcaaaaa caggaaggca aaatgccgca aaaaagggaa taagggcgac acggaaatgt  7320
tgaatactca tactcttcct ttttcaatat tattgaagca tttatcaggg ttattgtctc  7380
atgagcggat acatatttga atgtatttag aaaaataaac aaataggggt tccgcgcaca  7440
tttccccgaa aagtgccacc tgacgtc                                      7467
```

```
SEQ ID NO: 5           moltype = DNA  length = 10
FEATURE                Location/Qualifiers
misc_feature           1..10
                       note = Kozac motif vetebrates
source                 1..10
                       mol_type = other DNA
                       organism = synthetic construct
SEQUENCE: 5
gccrccatgg                                                         10
```

```
SEQ ID NO: 6           moltype = DNA  length = 3822
FEATURE                Location/Qualifiers
source                 1..3822
                       mol_type = other DNA
                       note = sars cov 2 isolate Wuhan Hu 1
                       organism = SARS COV2
CDS                    1..3822
SEQUENCE: 6
atgtttgttt ttcttgtttt attgccacta gtctctagtc agtgtgttaa tcttacaacc  60
agaactcaat taccccctgc atacactaat tctttcacac gtggtgttta ttaccctgac  120
aaagttttca gatcctcagt tttacattca actcaggact tgttcttacc tttcttttcc  180
aatgttactt ggttccatgc tatacatgtc tctgggacca atggtactaa gaggtttgat  240
aaccctgtcc taccatttaa tgatggtgtt tattttgctt ccactgagaa gtctaacata  300
ataagaggct ggatttttgg tactacttta gattcgaaga cccagtccct acttattgtt  360
aataacgcta ctaatgttgt tattaaagtc tgtgaatttc aattttgtaa tgatccattt  420
ttgggtgttt attaccacaa aaacaacaaa agttggatgg aaagtgagtt cagagtttat  480
tctagtgcga ataattgcac ttttgaatat gtctctcagc cttttcttat ggaccttgaa  540
ggaaaacagg gtaatttcaa aaatcttagg gaatttgtgt ttaagaatat tgatggttat  600
tttaaaatat attctaagca cacgcctatt aatttagtgc gtgatctccc tcagggtttt  660
tcggctttag aaccattggt agatttgcca ataggtatta acatcactag gtttcaaact  720
ttacttgctt tacatagaag ttatttgact cctggtgatt cttcttcagg ttggacagct  780
ggtgctgcag cttattatgt gggttatctt caacctagga cttttctatt aaaatataat  840
gaaaatggaa ccattacaga tgctgtagac tgtgcacttg accctctctc agaaacaaag  900
tgtacgttga aatccttcac tgtagaaaaa ggaatctatc aaacttctaa ctttagagtc  960
caaccaacag aatctattgt tagatttcct aatattacaa acttgtgccc ttttggtgaa  1020
gtttttaacg ccaccagatt tgcatctgtt tatgcttgga acaggaagag aatcagcaac  1080
tgtgttgctg attattctgt cctatataat tccgcatcat tttccacttt taagtgttat  1140
ggagtgtctc ctactaaatt aaatgatctc tgctttacta atgtctatgc agattcattt  1200
gtaattagag gtgatgaagt cagacaaatc gctccagggc aaactggaaa gattgctgat  1260
tataattata aattaccaga tgattttaca ggctgcgtta tagcttggaa ttctaacaat  1320
cttgattcta aggttggtgg taattataat tacctgtata gattgtttag gaagtctaat  1380
ctcaaacctt ttgagagaga tatttcaact gaaatctatc aggccggtag cacaccttgt  1440
aatggtgttg aaggttttaa ttgttacttt cctttacaat catatggttt ccaacccact  1500
```

-continued

```
aatggtgttg gttaccaacc atacagagta gtagtacttt cttttgaact tctacatgca  1560
ccagcaactg tttgtggacc taaaaagtct actaatttgg ttaaaaacaa atgtgtcaat  1620
ttcaacttca atggtttaac aggcacaggt gttcttactg agtctaacaa aaagtttctg  1680
cctttccaac aatttggcag agacattgct gacactactg atgctgtccg tgatccacag  1740
acacttgaga ttcttgacat tacaccatgt tcttttggtg gtgtcagtgt tataacacca  1800
ggaacaaata cttctaacca ggttgctgtt ctttatcagg atgttaactg cacagaagtc  1860
cctgttgcta ttcatgcaga tcaacttact cctacttggc gtgtttattc tacaggttct  1920
aatgtttttc aaacacgtgc aggctgttta ataggggctg aacatgtcaa caactcatat  1980
gagtgtgaca tacccattgg tgcaggtata tgcgctagtt atcagactca gactaattct  2040
cctcggcggg cacgtagtgt agctagtcaa tccatcattg cctacactat gtcacttggt  2100
gcagaaaatt cagttgctta ctctaataac tctattgcca tacccacaaa ttttactatt  2160
agtgttacca cagaaattct accagtgtct atgaccaaga catcagtaga ttgtacaatg  2220
tacatttgtg gtgattcaac tgaatgcagc aatcttttgt tgcaatatgg cagtttttgt  2280
acacaattaa accgtgcttt aactggaata gctgttgaac aagacaaaaa cacccaagaa  2340
gtttttgcac aagtcaaaca aatttacaaa acaccaccaa ttaaagattt tggtggtttt  2400
aatttttcac aaatattacc agatccatca aaaccaagca agaggtcatt tattgaagat  2460
ctacttttca acaaagtgac acttgcagat gctggcttca tcaaacaata tggtgattgc  2520
cttggtgata ttgctgctag agacctcatt tgtgcacaaa agtttaacgg ccttactgtt  2580
ttgccacctt tgctcacaga tgaaatgatt gctcaataca cttctgcact gttagcgggt  2640
acaatcactt ctggttggac ctttggtgca ggtgctgcat tacaaatacc atttgctatg  2700
caaatggctt ataggtttaa tggtattgga gttacacaga atgttctcta tgagaaccaa  2760
aaattgattg ccaaccaatt taatagtgct attggcaaaa ttcaagactc actttcttcc  2820
acagcaagtg cacttggaaa acttcaagat gtggtcaacc aaaatgcaca agctttaaac  2880
acgcttgtta aacaacttag ctccaatttt ggtgcaattt caagtgtttt aaatgatatc  2940
ctttcacgtc ttgacaaagt tgaggctgaa gtgcaaattg ataggttgat cacaggcaga  3000
cttcaaagtt tgcagacata tgtgactcaa caattaatta gagctgcaga aatcagagct  3060
tctgctaatc ttgctgctac taaaatgtca gagtgtgtac ttggacaatc aaaaagagtt  3120
gattttgtg gaaagggcta tcatcttatg tccttccctc agtcagcacc tcatggtgta  3180
gtcttcttgc atgtgactta tgtccctgca caagaaaaga acttcacaac tgctcctgcc  3240
atttgtcatg atggaaaagc acactttcct cgtgaaggtg tctttgtttc aaatggcaca  3300
cactggtttg taacacaaag gaatttttat gaaccacaaa tcattactac agacaacaca  3360
tttgtgtctg gtaactgtga tgttgtaata ggaattgtca acaacacagt ttatgatcct  3420
ttgcaacctg aattagactc attcaaggag gagttagata aatattttaa gaatcataca  3480
tcaccagatg ttgatttagg tgacatctct ggcattaatg cttcagttgt aaacattcaa  3540
aaagaaattg accgcctcaa tgaggttgcc aagaatttaa atgaatctct catcgatctc  3600
caagaacttg gaaagtatga gcagtatata aaatggccat ggtacatttg gctaggtttt  3660
atagctggct tgattgccat agtaatggtg acaattatgc tttgctgtat gaccagttgc  3720
tgtagttgtc tcaagggctg ttgttcttgt ggatcctgct gcaaatttga tgaagacgac  3780
tctgagccag tgctcaaagg agtcaaatta cattacacat aa                    3822

SEQ ID NO: 7           moltype = AA  length = 1273
FEATURE                Location/Qualifiers
source                 1..1273
                       mol_type = protein
                       note = SARS COV 2 Wuhan Hu 1
                       organism = SARS COV 2
SEQUENCE: 7
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                    1273
```